(12) United States Patent
Abrecht et al.

(10) Patent No.: US 7,772,264 B2
(45) Date of Patent: Aug. 10, 2010

(54) SALT AND POLYMORPHS OF A DPPIV INHIBITOR

(75) Inventors: Stefan Abrecht, Duggingen (CH);
Andre Gerard Bubendorf, Uffheim (FR); Stephan Goetzoe, Muttenz (CH); Olaf Grassmann, Kandern (DE); Francois Montavon, Delemont (CH); Regina Moog, Freiburg (DE); Franziska Rohrer, Riehen (CH); Armin Ruf, Freiburg (DE); Michelangelo Scalone, Birsfelden (CH); Urs Schwitter, Reinach (CH); Shaoning Wang, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 351 days.

(21) Appl. No.: 11/376,862

(22) Filed: Mar. 16, 2006

(65) Prior Publication Data
US 2006/0217428 A1 Sep. 28, 2006

(30) Foreign Application Priority Data
Mar. 22, 2005 (EP) .................. 05102251

(51) Int. Cl.
*A61K 31/42* (2006.01)
*A61K 31/40* (2006.01)
*C07D 263/34* (2006.01)
*C07D 207/09* (2006.01)

(52) U.S. Cl. .................. 514/374; 514/422; 548/236; 548/518

(58) Field of Classification Search .................. 514/374, 514/422; 548/236, 518
See application file for complete search history.

(56) References Cited

U.S. PATENT DOCUMENTS 6,043,366 A * 3/2000 Adam et al. .................. 546/16
6,673,815 B2 * 1/2004 Devasthale et al. .......... 514/325

FOREIGN PATENT DOCUMENTS

| EP | 0 922 503 | 4/2000 |
|---|---|---|
| WO | WO 03/037327 | 5/2003 |
| WO | WO 03/037327 A1 * | 5/2003 |
| WO | WO 2004/020407 | 3/2004 |

OTHER PUBLICATIONS

Putochin, N. CAS Accession No. 1927:552.*
Bauer et al. "Ritonavir: An Extrordinary Example of Conformational Polymorphism" Pharmaceutical Research, 2001, vol. 18, No. 6, pp. 859-866.*

* cited by examiner

*Primary Examiner*—Joseph R Kosack
(74) *Attorney, Agent, or Firm*—George W. Johnston; Dennis P. Tramaloni; Samuel H. Megerditchian

(57) ABSTRACT

The invention is concerned with (S)-1-{[2-(5-Methyl-2-phenyl-oxazol-4-yl)-ethylamino]-acetyl}-pyrrolidine-2-carbonitrile mesylate and crystalline polymorphs of this compound. This compound and its polymorphic forms exhibits superior properties compared to the previously known compounds and can be used as medicament for the treatment of disorders which are associated with DPP-IV.

5 Claims, 10 Drawing Sheets

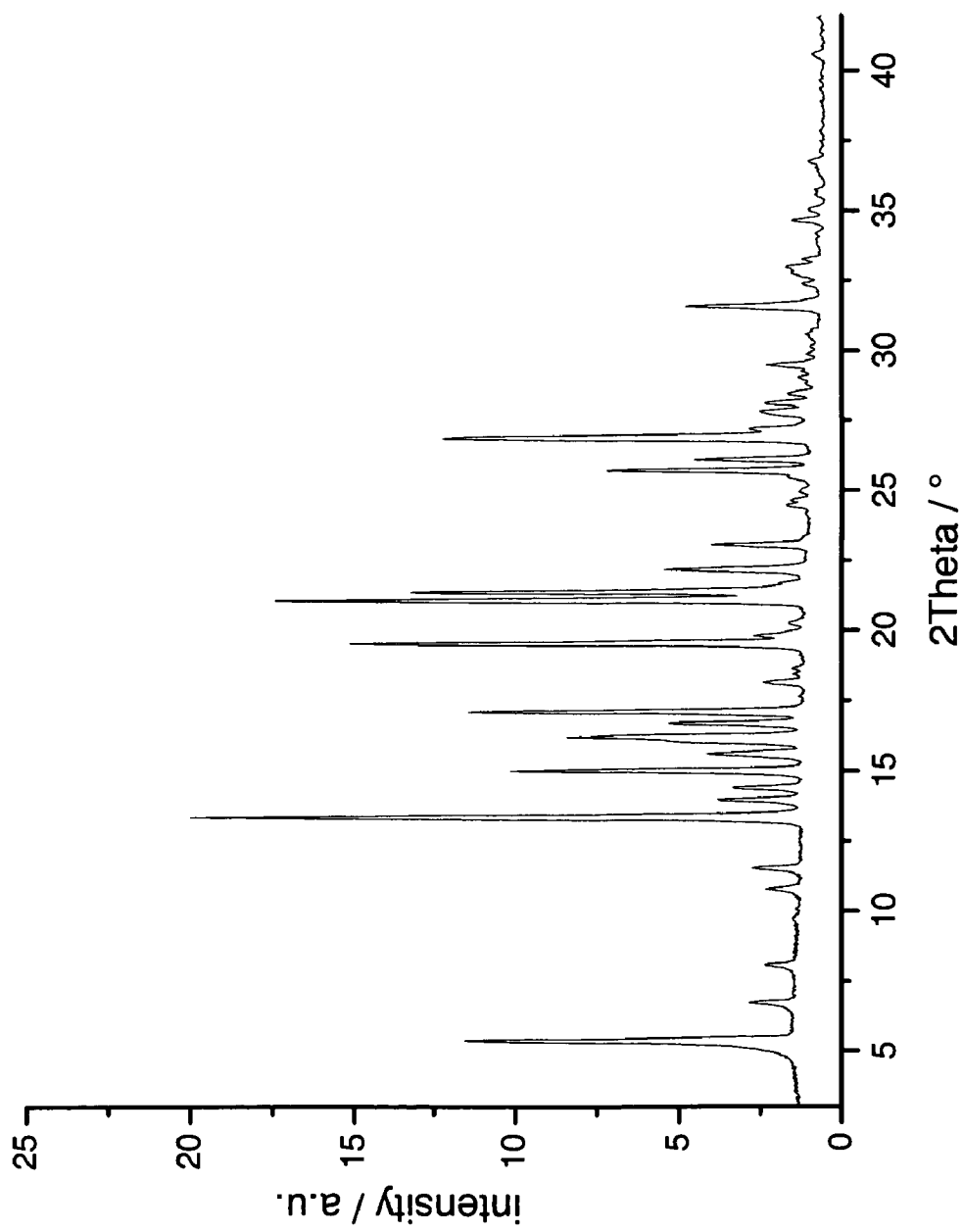
Figure 1: X-ray diffraction pattern of polymorph A

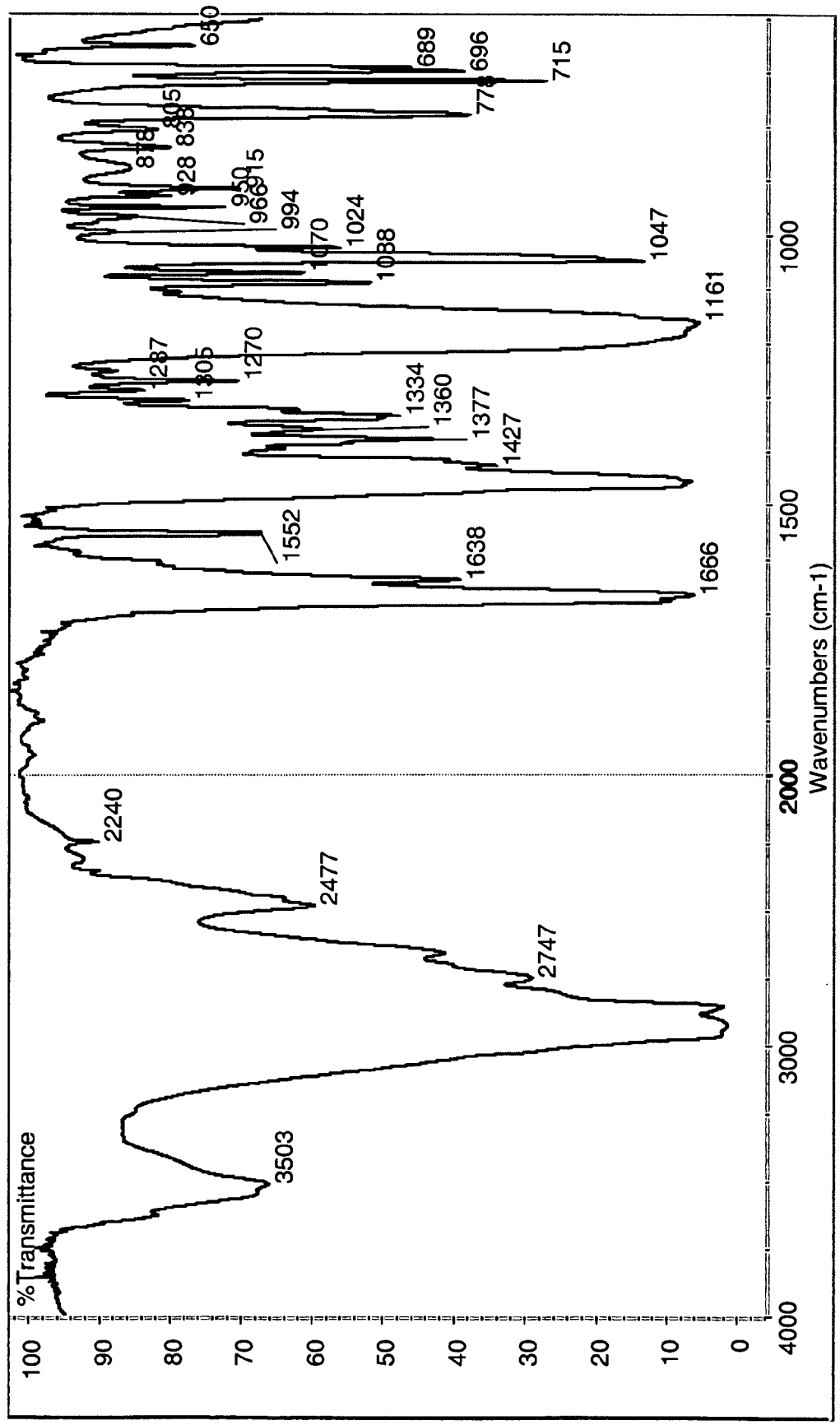
Figure 2: IR-spectrum of polymorph A

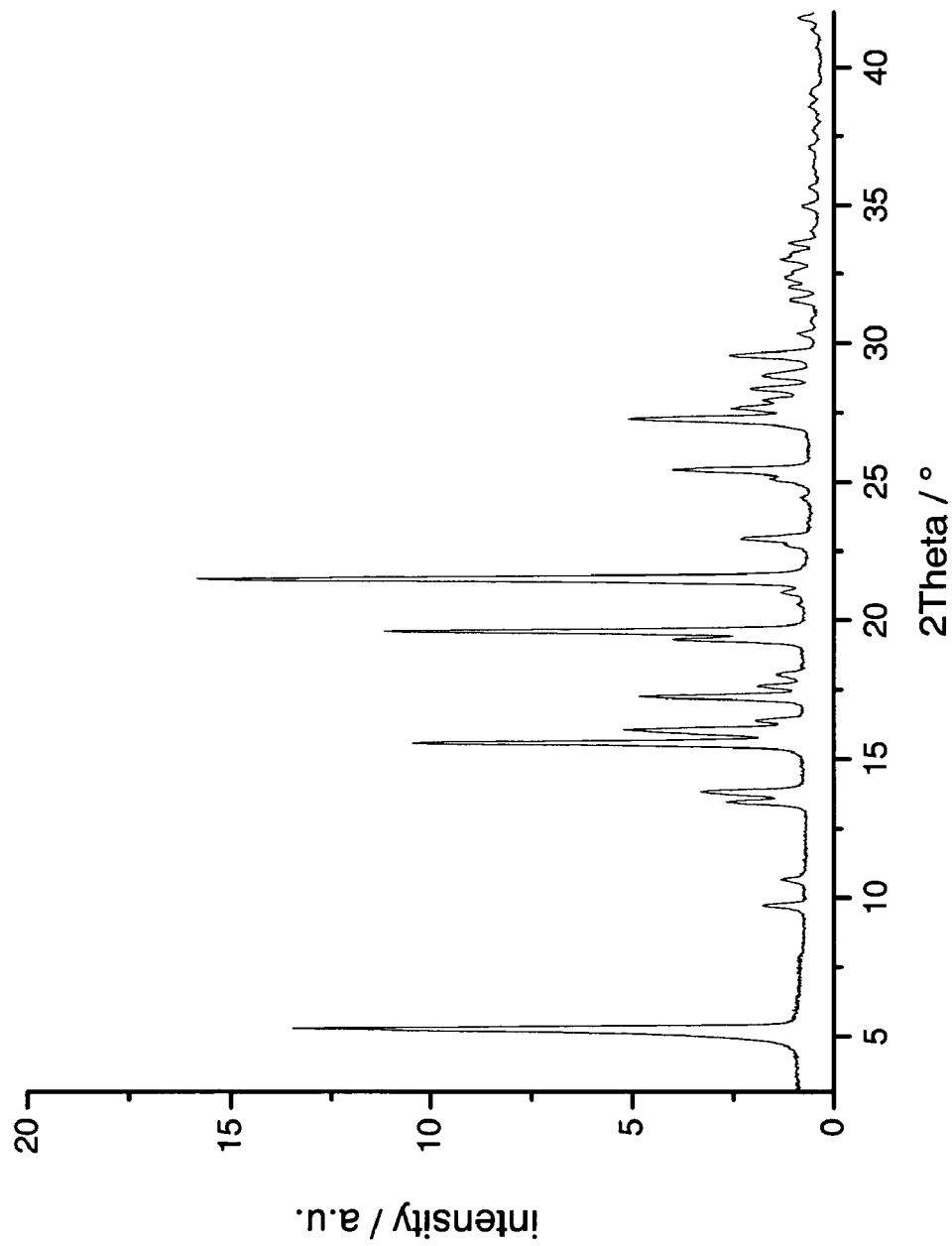
Figure 3: X-ray diffraction pattern of polymorph B

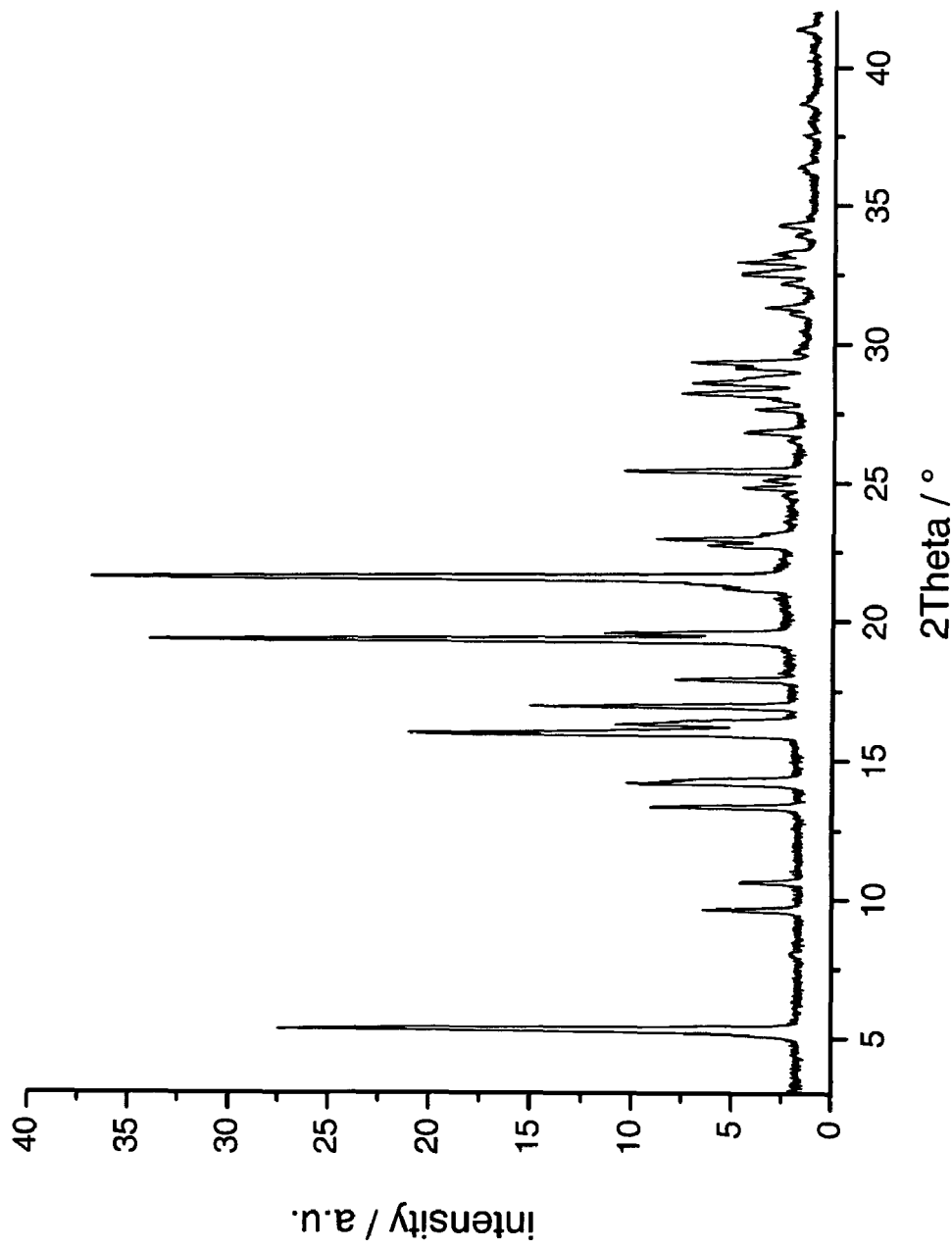
Figure 4: X-ray diffraction pattern of polymorph B

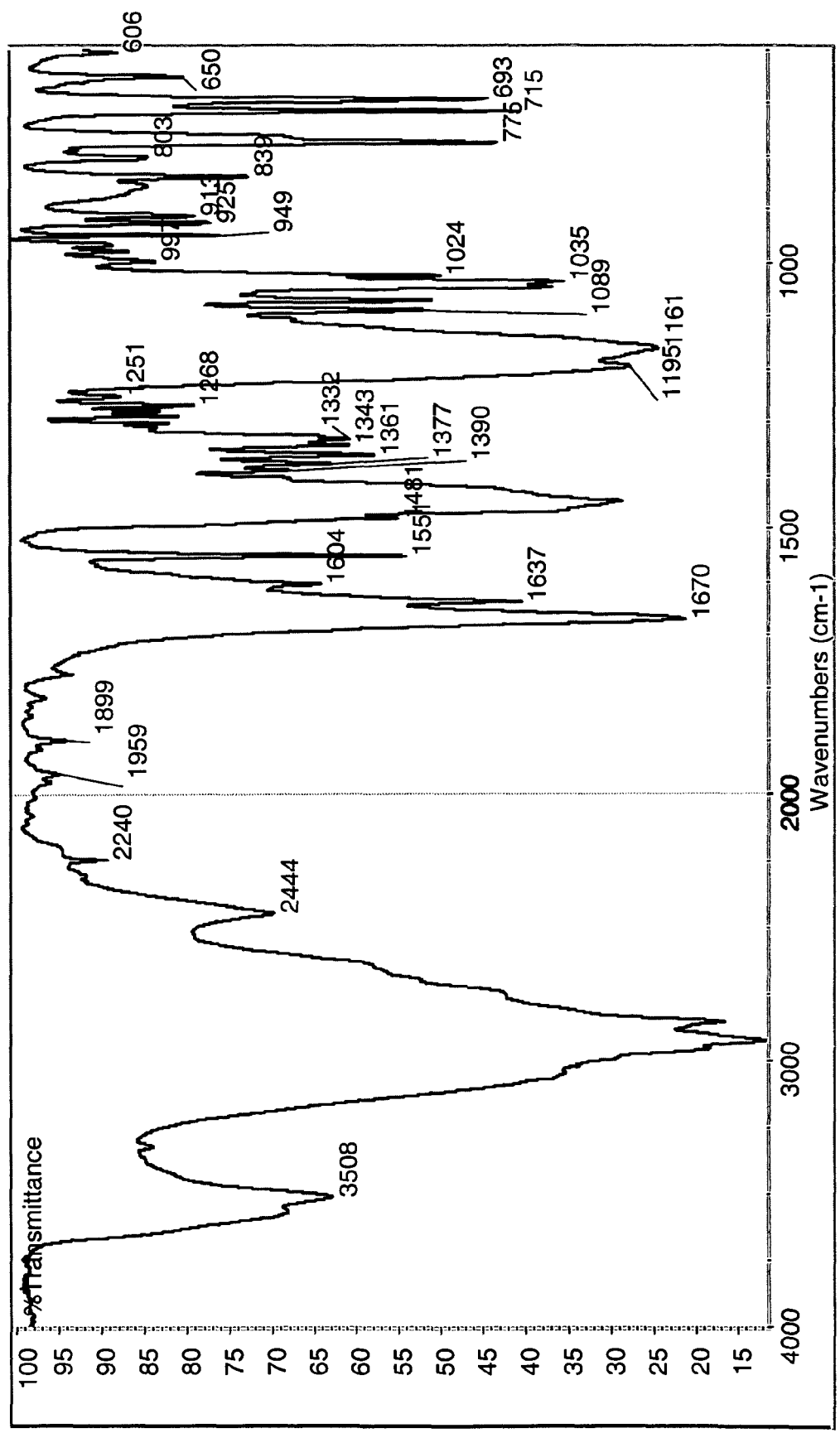
Figure 5: IR-spectrum of polymorph B

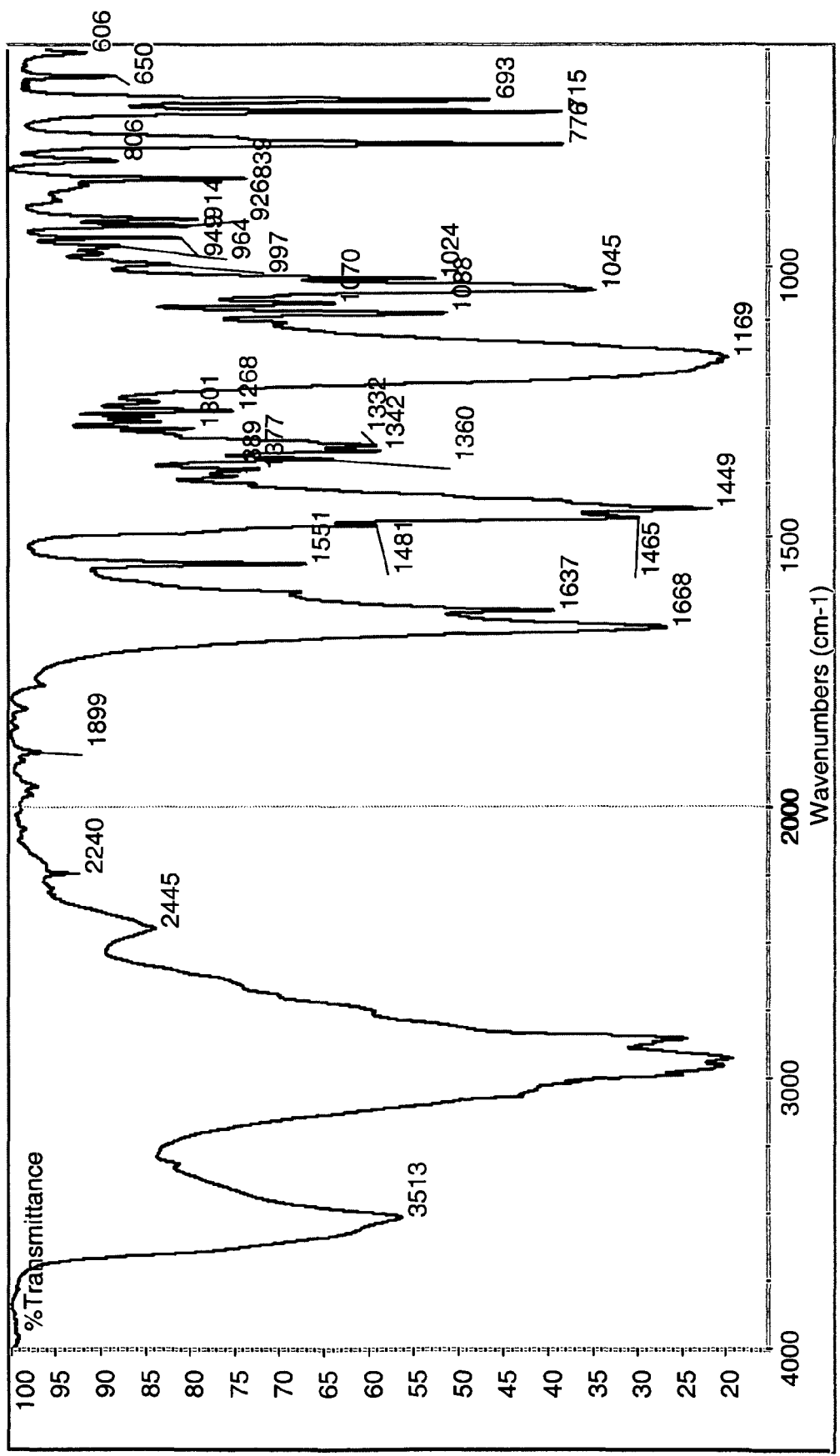
Figure 6: IR-spectrum of polymorph B

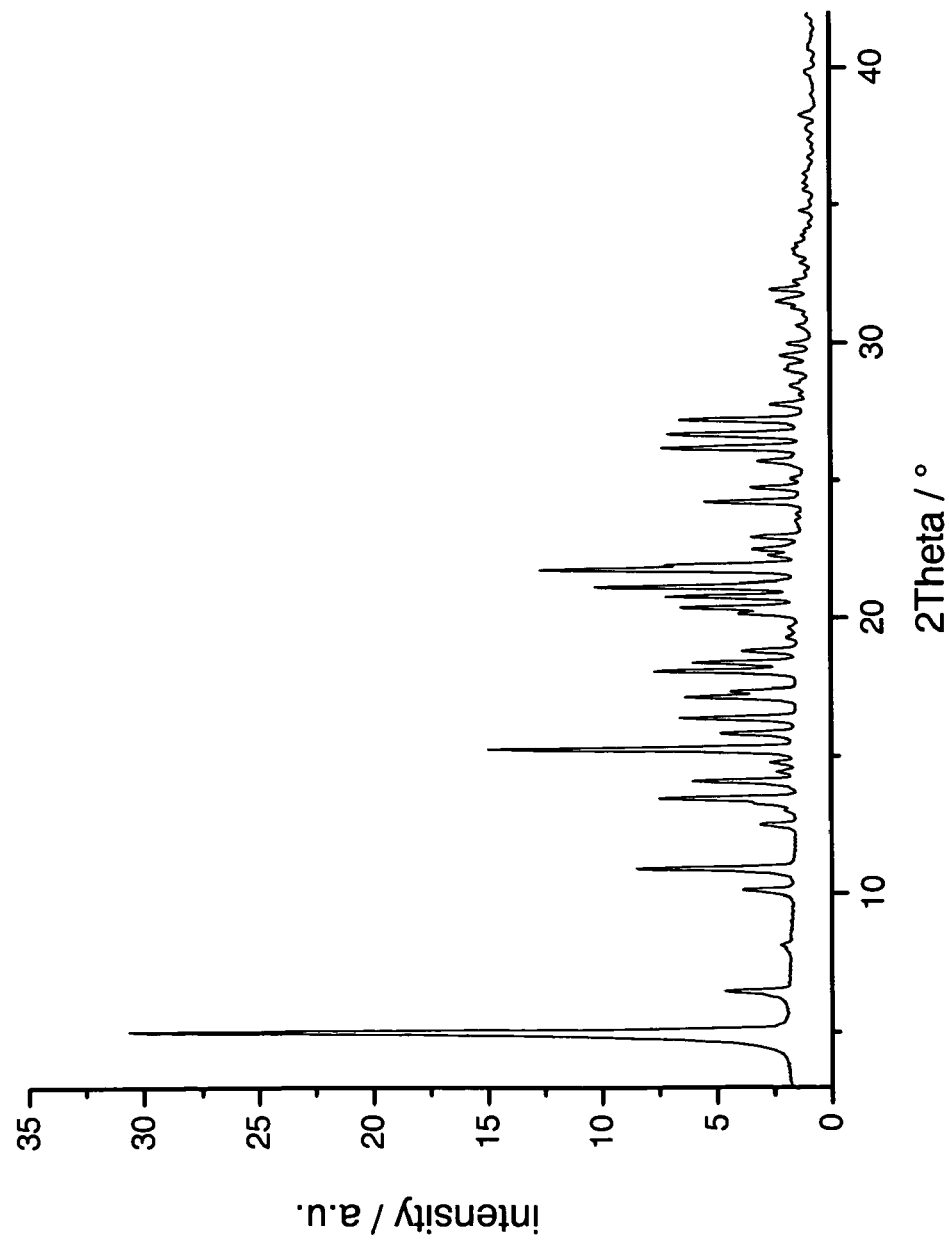
Figure 7: X-ray diffraction pattern of polymorph C

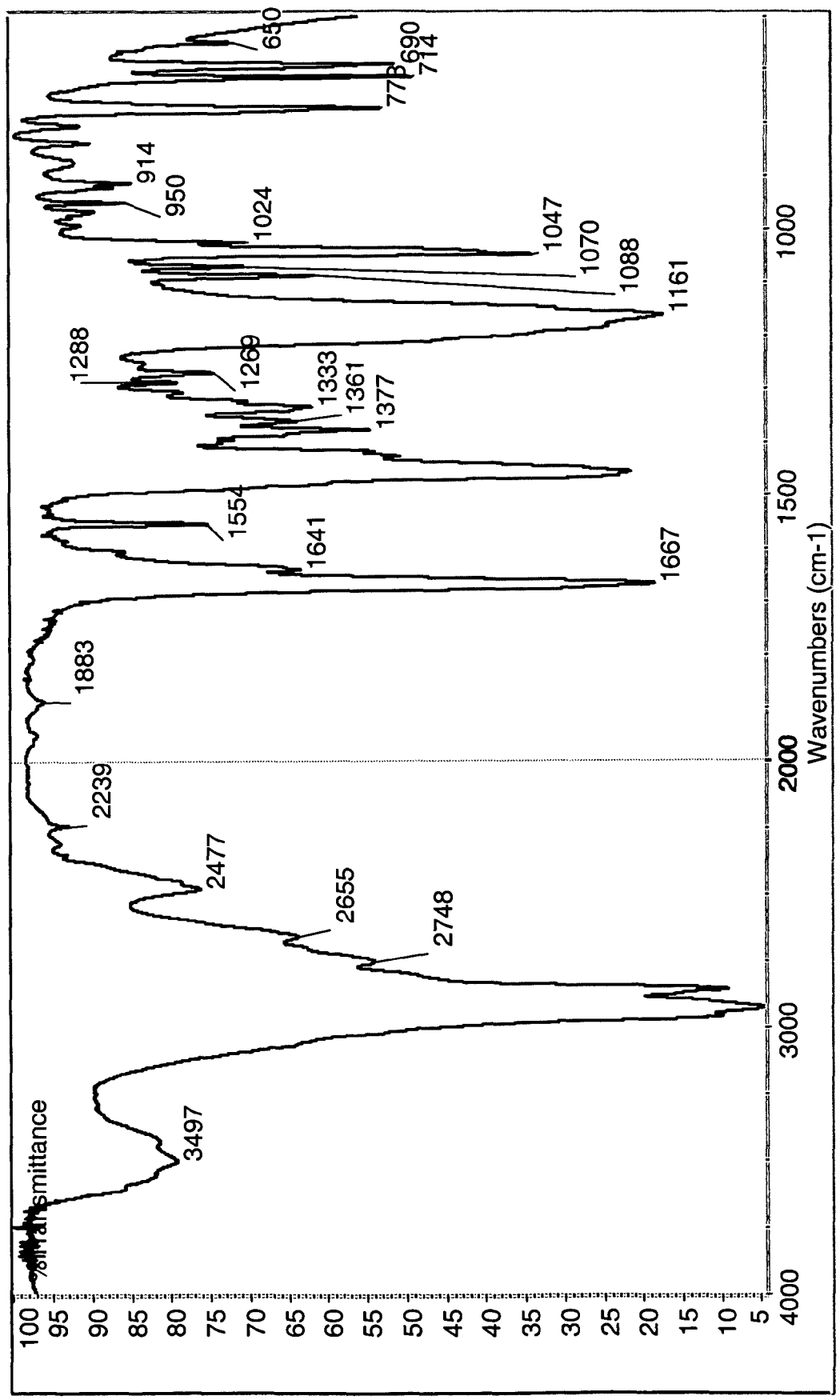
Figure 8: IR-spectrum of polymorph C

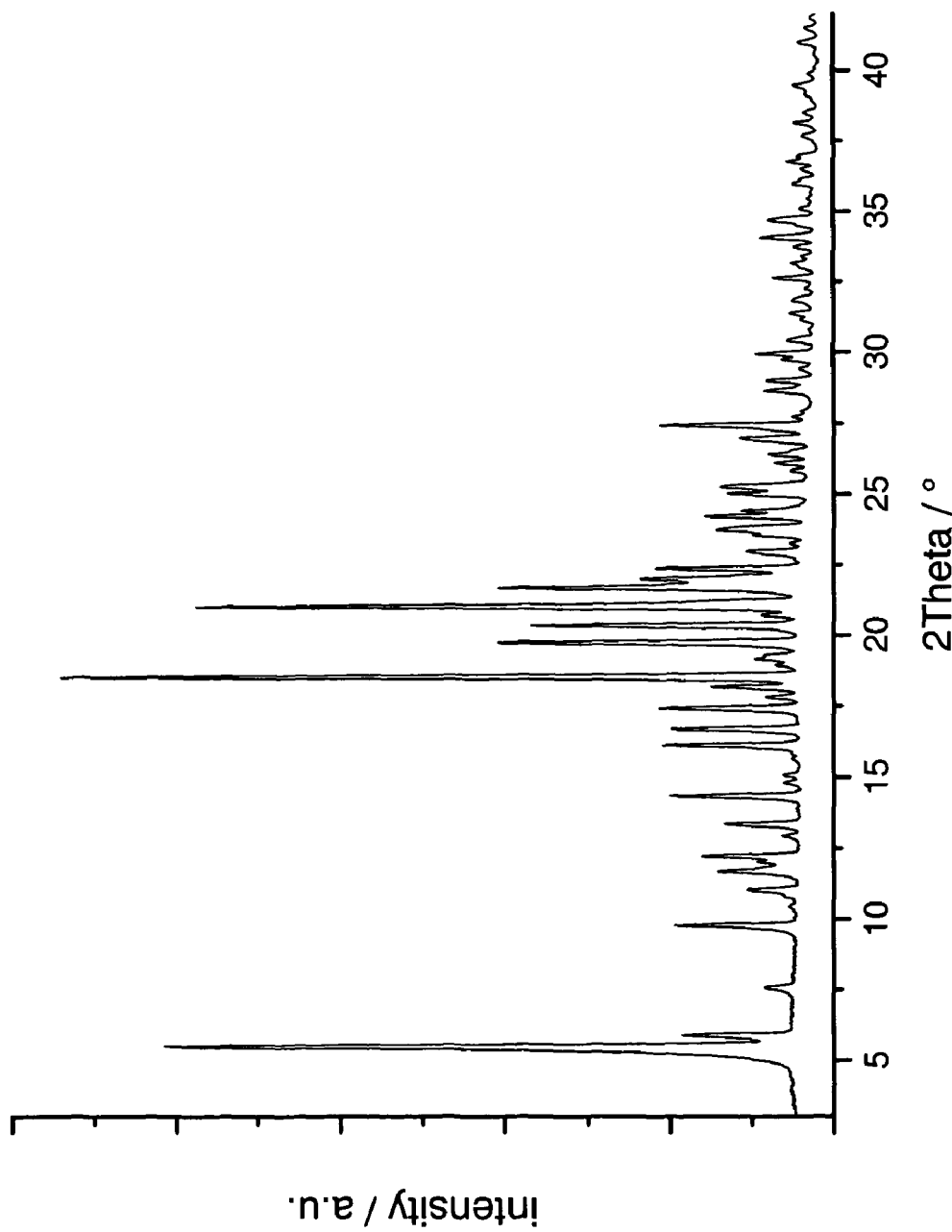
Figure 9: X-ray diffraction pattern of polymorph D

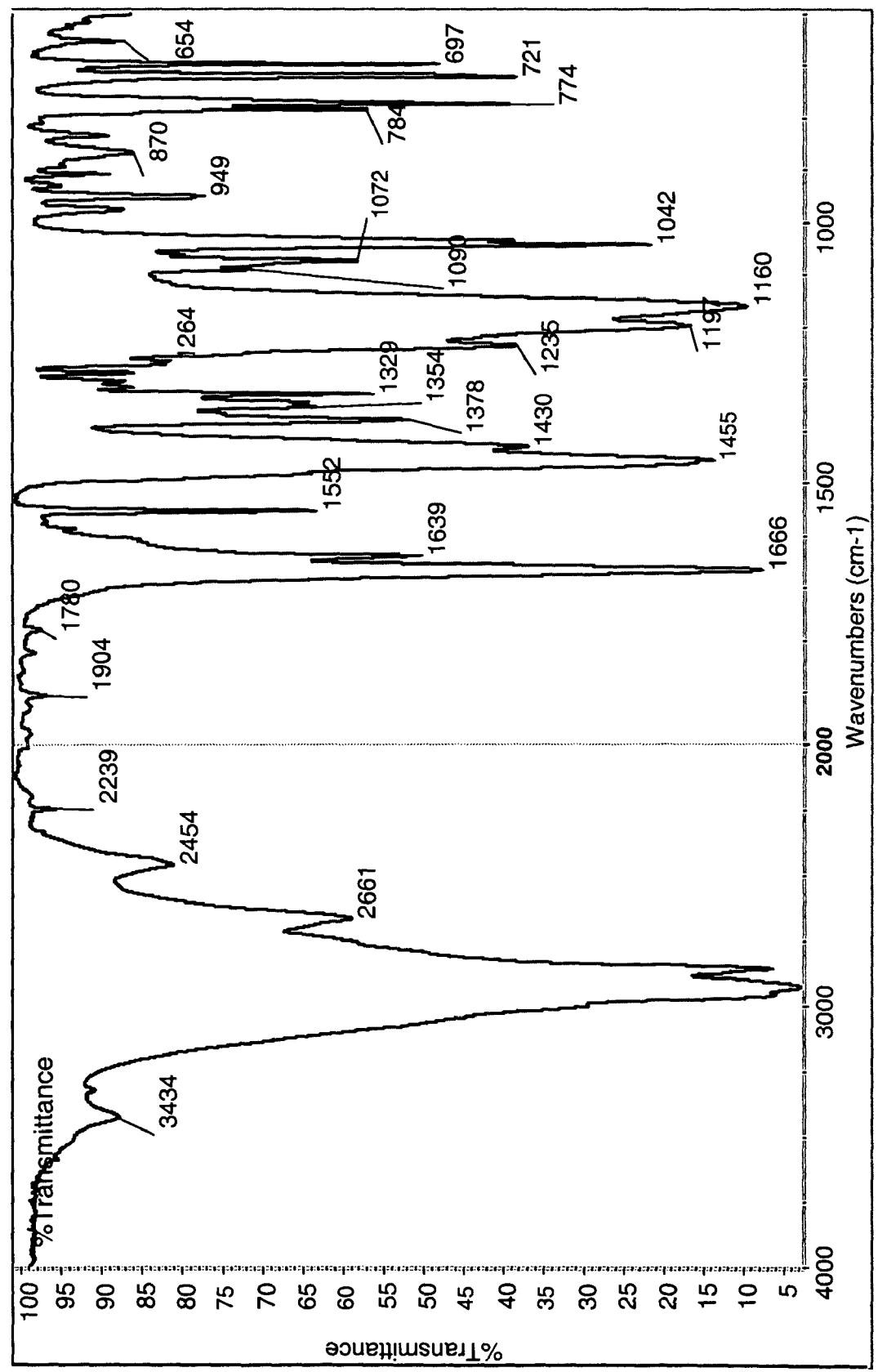
Figure 10: IR-spectrum of polymorph D

SALT AND POLYMORPHS OF A DPPIV INHIBITOR

PRIORITY TO RELATED APPLICATIONS

This application claims the benefit of European Application No. 05102251.5, filed Mar. 22, 2005, which is hereby incorporated by reference in its entirety.

FIELD OF THE INVENTION

The present invention is directed to a salt of (S)-1-{[2-(5-Methyl-2-phenyl-oxazol-4-yl)-ethylamino]-acetyl}-pyrrolidine-2-carbonitrile, particularly (S)-1-{[2-(5-Methyl-2-phenyl-oxazol-4-yl)-ethylamino]-acetyl}-pyrrolidine-2-carbonitrile mesylate, which exhibits unexpected advantages compared to (S)-1-{[2-(5-Methyl-2-phenyl-oxazol-4-yl)-ethylamino]-acetyl}-pyrrolidine-2-carbonitrile. The invention is also directed to three crystalline polymorphs of (S)-1-{[2-(5-Methyl-2-phenyl-oxazol-4-yl)-ethylamino]-acetyl}-pyrrolidine-2-carbonitrile mesylate, which also exhibit unexpected advantages.

All documents cited or relied upon below are expressly incorporated herein by reference.

BACKGROUND

The compound (S)-1-{[2-(5-Methyl-2-phenyl-oxazol-4-yl)-ethylamino]-acetyl}-pyrrolidine-2-carbonitrile is useful in the prophylaxis and/or treatment of diseases which are related with the enzyme dipeptidyl peptidase IV (EC.3.4.14.5, abbreviated in the following as DPP-IV). In WO 03/037327, the preparation of (S)-1-{[2-(5-Methyl-2-phenyl-oxazol-4-yl)-ethylamino]-acetyl}-pyrrolidine-2-carbonitrile as well as the uses of this compound have been disclosed. In particular, (S)-1-{[2-(5-Methyl-2-phenyl-oxazol-4-yl)-ethylamino]-acetyl}-pyrrolidine-2-carbonitrile is an inhibitor of DPP-IV and can be used for the treatment and/or prevention of diseases which are associated with DPP-IV, such as diabetes, particularly non-insulin dependent diabetes mellitus, impaired glucose tolerance, bowl disease, colitis ulcerosa, morbus crohn, obesity, and/or metabolic syndrome. The compound can further be used as a diuretic agent or for use as therapeutic active substances for the treatment and/or prophylaxis of hypertension. (S)-1-{[2-(5-Methyl-2-phenyl-oxazol-4-yl)-ethylamino]-acetyl}-pyrrolidine-2-carbonitrile is characterized by formula (I):

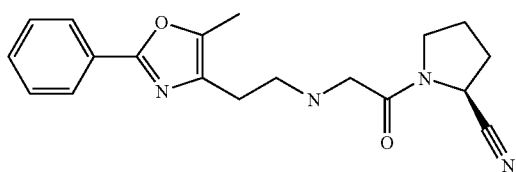

(I)

Polymorphism is defined as the ability of a substance to crystallize in more than one crystal lattice arrangement. Polymorphism can influence many aspects of solid state properties of a drug. Different crystal modifications of a substance may differ considerably from one another in many respects such as their solubility, dissolution rate and finally bioavailability. An exhaustive treatment of polymorphism in pharmaceutical and molecular crystals is given e.g. by Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

SUMMARY OF THE INVENTION

In an embodiment of the present invention, provided is the compound (S)-1-{[2-(5-Methyl-2-phenyl-oxazol-4-yl)-ethylamino]-acetyl}-pyrrolidine-2-carbonitrile mesylate.

In other embodiments of the present invention, provided are crystalline polymorphs of the compound (S)-1-{[2-(5-Methyl-2-phenyl-oxazol-4-yl)-ethylamino]-acetyl}-pyrrolidine-2-carbonitrile mesylate.

In a further embodiment of the present invention, provided is a process for the manufacture of (S)-1-{[2-(5-Methyl-2-phenyl-oxazol-4-yl)-ethylamino]-acetyl}-pyrrolidine-2-carbonitrile mesylate or crystalline polymorphs thereof, which process comprises reacting a compound of formula (II)

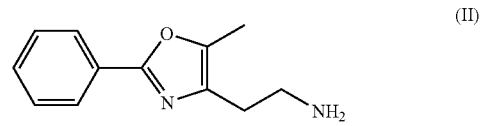

(II)

with a compound of formula (III)

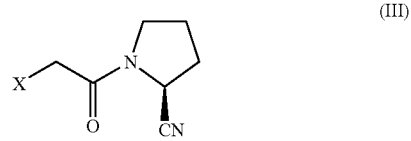

(III)

in the presence of Ca(OH)$_2$, wherein X is a leaving group.

In a yet another embodiment of the present invention, provided is a pharmaceutical composition, comprising a therapeutically effective amount of a compound or crystalline polymorph of (S)-1-{[2-(5-Methyl-2-phenyl-oxazol-4-yl)-ethylamino]-acetyl}-pyrrolidine-2-carbonitrile mesylate and a pharmaceutically acceptable carrier and/or adjuvant.

In a still further embodiment of the present invention, provided is a method for the treatment and/or prophylaxis of diseases which are associated with DPP-IV such as diabetes, non-insulin dependent diabetes mellitus, impaired glucose tolerance, bowl disease, colitis ulcerosa, morbus crohn, obesity, and/or metabolic syndrome, comprising the step of administering a therapeutically effective amount of a compound or crystalline polymorph of (S)-1-{[2-(5-Methyl-2-phenyl-oxazol-4-yl)-ethylamino]-acetyl}-pyrrolidine-2-carbonitrile mesylate to a human being or animal in need thereof.

BRIEF DESCRIPTION OF THE DRAWINGS

FIG. 1 is a X-ray diffraction pattern of polymorph A.
FIG. 2 is an IR-spectrum of polymorph A.
FIG. 3 is a X-ray diffraction pattern of polymorph B.
FIG. 4 is a X-ray diffraction pattern of polymorph B.
FIG. 5 is an IR-spectrum of polymorph B.
FIG. 6 is an IR-spectrum of polymorph B.

FIG. 7 is a X-ray diffraction pattern of polymorph C.
FIG. 8 is an IR-spectrum of polymorph C.
FIG. 9 is a X-ray diffraction pattern of polymorph D.
FIG. 10 is an IR-spectrum of polymorph D.

DETAILED DESCRIPTION

The present invention has found that (S)-1-{[2-(5-Methyl-2-phenyl-oxazol-4-yl)-ethylamino]-acetyl}-pyrrolidine-2-carbonitrile mesylate exhibits various unexpected advantages, e.g. in context with chemical stability, mechanical properties, processability, solubility, dissolution, bioavailability, toxicology or pharmacokinetic properties.

Also, the invention has found that (S)-1-{[2-(5-Methyl-2-phenyl-oxazol-4-yl)-ethylamino]-acetyl}-pyrrolidine-2-carbonitrile mesylate can exist in four polymorphic forms, designated as polymorph A, polymorph B, polymorph C and polymorph D, which exhibit various unexpected advantages, e.g. in context with chemical stability, mechanical properties, processability, solubility, dissolution, bioavailability or pharmacokinetic properties.

Thus, the present invention provides the novel compound (S)-1-{[2-(5-Methyl-2-phenyl-oxazol-4-yl)-ethylamino]-acetyl}-pyrrolidine-2-carbonitrile mesylate and three novel crystalline polymorphs of (S)-1-{[2-(5-Methyl-2-phenyl-oxazol-4-yl)-ethylamino]-acetyl}-pyrrolidine-2-carbonitrile mesylate, which unexpectedly exhibit desirable and improved pharmacological properties when compared to the known compound (S)-1-{[2-(5-Methyl-2-phenyl-oxazol-4-yl)-ethylamino]-acetyl}-pyrrolidine-2-carbonitrile.

Unless otherwise indicated, the following definitions are set forth to illustrate and define the meaning and scope of the various terms used to describe the invention herein.

The term "crystalline polymorph" or "polymorph" refers to a crystal form or modification which can be characterized by analytical methods such as e.g. X-ray powder diffraction or IR-spectroscopy.

The term "polymorph A" relates to a specific crystalline polymorph of (S)-1-{[2-(5-Methyl-2-phenyl-oxazol-4-yl)-ethylamino]-acetyl}-pyrrolidine-2-carbonitrile mesylate as defined below.

The term "polymorph B" relates to a specific crystalline polymorph of (S)-1-{[2-(5-Methyl-2-phenyl-oxazol-4-yl)-ethylamino]-acetyl}-pyrrolidine-2-carbonitrile mesylate as defined below.

The term "polymorph C" relates to a specific crystalline polymorph of (S)-1-{[2-(5-Methyl-2-phenyl-oxazol-4-yl)-ethylamino]-acetyl}-pyrrolidine-2-carbonitrile mesylate as defined below.

The term "polymorph D" relates to a specific crystalline polymorph of (S)-1-{[2-(5-Methyl-2-phenyl-oxazol-4-yl)-ethylamino]-acetyl}-pyrrolidine-2-carbonitrile mesylate as defined below.

The term "IR" means infrared.

In detail, the present invention relates to the compound (S)-1-{[2-(5-Methyl-2-phenyl-oxazol-4-yl)-ethylamino]-acetyl}-pyrrolidine-2-carbonitrile mesylate.

Furthermore, the present invention relates to a crystalline polymorph of the compound as described above, which is characterized by an X-ray powder diffraction pattern having characteristic peaks expressed in degrees 2-theta at approximately

| degree 2-theta |
| --- |
| 5.4 |
| 13.3 |
| 15.0 |
| 17.1 |
| 19.5 |
| 21.1 |
| 21.4 |
| 26.9 |

This polymorph is referred to as "polymorph A". The term "approximately" means in this context that there is an uncertainty in the measurements of the degrees 2-theta of +0.2 (expressed in degrees 2-theta).

Preferably, the crystalline polymorph A as defined above is characterized by the X-ray powder diffraction pattern shown in FIG. 1.

The crystalline polymorph A as described above can also be characterized by its IR-spectrum. The present invention therefore also relates to a crystalline polymorph of the compound as defined above, which is characterized by an IR absorption spectrum having characteristic peaks expressed in $cm^{-1}$ at approximately 3503 $cm^{-1}$, 2747 $cm^{-1}$, 2649 $cm^{-1}$, 2477 $cm^{-1}$, 2240 $cm^{-1}$, 1666 $cm^{-1}$, 1638 $cm^{-1}$, 1552 $cm^{-1}$, 1427 $cm^{-1}$, 1377 $cm^{-1}$, 1360 $cm^{-1}$, 1334 $cm^{-1}$, 1305 $cm^{-1}$, 1270 $cm^{-1}$, 1161 $cm^{-1}$, 1088 $cm^{-1}$, 1070 $cm^{-1}$, 1047 $cm^{-1}$, 1024 $cm^{-1}$, 944 $cm^{-1}$, 966 $cm^{-1}$, 950 $cm^{-1}$, 915 $cm^{-1}$, 878 $cm^{-1}$, 838 $cm^{-1}$, 805 $cm^{-1}$, 778 $cm^{-1}$, 715 $cm^{-1}$, 696 $cm^{-1}$, 689 $cm^{-1}$, 650 $cm^{-1}$. The term "approximately" means in this context that the $cm^{-1}$ values can vary, e.g. by up to $\pm 1$ $cm^{-1}$. Preferably, the crystalline polymorph A as described above, is characterized by the IR absorption spectrum shown in FIG. 2.

Another embodiment of the present invention is related to a crystalline polymorph of the compound as defined above, which is characterized by an X-ray powder diffraction pattern having characteristic peaks expressed in degrees 2-theta at approximately

| degree 2-theta |
| --- |
| 5.3 |
| 9.7 |
| 10.7 |
| 21.5 |
| 23.0 |
| 25.4 |

This polymorph is referred to as "polymorph B". The term "approximately" means in this context that there is an uncertainty in the measurements of the degrees 2-theta of $\pm 0.2$ (expressed in degrees 2-theta).

Preferably, the crystalline polymorph B as defined above is characterized by the x-ray powder diffraction pattern shown in FIG. 3 or FIG. 4.

The crystalline polymorph B as described above can also be characterized by its IR-spectrum. The present invention therefore also relates to a crystalline polymorph of the compound as defined above, which is characterized by the IR absorption spectrum shown in FIG. 5 or FIG. 6. The IR-spectrum in FIG. 5 exhibits characteristic peaks expressed in $cm^{-1}$ at approximately 3508 $cm^{-1}$, 2444 $cm^{-1}$, 2240 $cm^{-1}$, 1959 $cm^{-1}$, 1899 $cm^{-1}$, 1670 $cm^{-1}$, 1637 $cm^{-1}$, 1604 $cm^{-1}$, 1551 $cm^{-1}$, 1481 $cm^{-1}$, 1390 $cm^{-1}$, 1377 $cm^{-1}$, 1361 $cm^{-1}$, 1343 $cm^{-1}$, 1332 $cm^{-1}$, 1268 $cm^{-1}$, 1251 $cm^{-1}$, 1195 $cm^{-1}$, 1161 cm⁻¹, 1089 cm⁻¹, 1069 cm⁻¹, 1035 cm⁻¹, 997 cm⁻¹, 949 cm⁻¹, 925 cm⁻¹, 913 cm⁻¹, 839 cm⁻¹, 803, 775 cm⁻¹, 715 cm⁻¹, 693 cm⁻¹, 650 cm⁻¹. The IR-spectrum in FIG. 6 exhibits characteristic peaks expressed in cm⁻¹ at approximately 3513 cm⁻¹, 2245 cm⁻¹, 1959 cm⁻¹, 1899 cm⁻¹, 1668 cm⁻¹, 1637 cm⁻¹, 1604 cm⁻¹, 1551 cm⁻¹, 1481 cm⁻¹, 1389 cm⁻¹, 1377 cm⁻¹, 1360 cm⁻¹, 1343 cm⁻¹, 1332 cm⁻¹, 1169 cm⁻¹, 1088 cm⁻¹, 1069 cm⁻¹, 1045 cm⁻¹, 997 cm⁻¹, 949 cm⁻¹, 926 cm⁻¹, 914 cm⁻¹, 839 cm⁻¹, 806 cm⁻¹, 776 cm⁻¹, 715 cm⁻¹, 693 cm⁻¹, 650 cm⁻¹. The term "approximately" means in this context that the cm⁻¹ values can vary, e.g. by up to ±1 cm⁻¹.

It has been observed that the polymorph B is hygroscopic and that the X-ray powder diffraction pattern and the IR-spectrum of polymorph B can vary, depending on the humidity of the analyzed sample. Water uptake and release, respectively, result in systematic shifts of some peak positions in the X-ray powder diffraction pattern. The crystal form B is characterized by a set of peaks, as described above, that are not susceptible to peak shifts in a range larger than 0.2 degrees in 2-theta. Samples of polymorph B, which have been dried, e.g. by elevated temperature or in a dry atmosphere, show the same X-ray powder diffraction pattern. In the IR spectrum of polymorph B, variations of humidity of the sample are mainly observed in following regions: 3700-3300, 1250-1150, 1045-1000 970-955, 900-850 cm⁻¹. However, changes of humidity can also have an influence on the position of the peaks outside these ranges.

FIG. 4 shows the X-ray powder diffraction pattern of a dried sample of polymorph B. FIG. 3 shows the X-ray powder diffraction pattern of a sample of polymorph B, which has been exposed to ambient humidity. FIG. 5 shows the IR-spectrum of a dried sample of polymorph B. FIG. 6 shows the IR-spectrum of a sample of polymorph B, which has been exposed to ambient humidity.

Polymorph B can also be characterized by its single crystal structure. The X-ray structures of a crystal of polymorph B under dry conditions and in ambient humidity demonstrate that both belong to the same space group P2₁ and have the same crystal packing and have crystal lattice parameters that differ less than 2%. Therefore the crystals are isomorphous. The occupancy of the hydrate water molecule was refined to 27% in the dried crystal and 59% in the crystal measured at ambient conditions. The only difference between the crystal structures of dried and ambient polymorph B is a slight rearrangement of the mesylate. The X-ray powder diffraction patterns calculated from the two crystal structures superimpose well with the corresponding experimental X-ray powder diffraction patterns measured from ambient and dried polymorph B. Crystal data from a dried and a humid single crystal of polymorph B are summarized in table 1 below.

TABLE 1

|  | Dried | Ambient humidity |
|---|---|---|
| Crystal system | monoclinic | monoclinic |
| Space Group | P2₁ | P2₁ |
| Molecules in unit cell | 2 | 2 |
| Cell axis a | 6.3970 Å | 6.4714 Å |
| Cell axis b | 11.003 Å | 10.836 Å |
| Cell axis c | 16.939 Å | 16.757 Å |
| Cell angles α, β, γ | 90.0°, 99.80°, 90.0° | 90.0°, 99.93°, 90.0° |
| Cell Volume | 1174.8 Å³ | 1157.6 Å³ |
| Density calculated | 1.241 g/cm³ | 1.274 g/cm³ |
| Temperature | 25° C. | 25° C. |
| Water occupancy | 27% | 59% |

In a further embodiment, the invention therefore relates to a crystalline polymorph of the compound as defined above, particularly polymorph B, which is characterized by the space group symmetry P2₁ and which comprises 2 molecules of the compound as defined above in the crystallographic unit cell, wherein the unit cell is characterized by the cell dimensions a, b and c, wherein a is from 6.2 Å to 6.7 Å, b is from 10.5 Å to 11.3 Å and c is from 16.3 Å to 17.4 Å, and the angles α, β and γ, wherein α is 90°, β is 99° to 101° and γ is 90°. Preferably, β is 99.5° to 100.4°.

Furthermore, the present invention relates to a crystalline polymorph of the compound as described above, which is characterized by an X-ray powder diffraction pattern having characteristic peaks expressed in degrees 2-theta at approximately

| degree 2-theta |
|---|
| 5.0 |
| 10.9 |
| 13.5 |
| 15.3 |
| 18.1 |
| 20.8 |
| 21.1 |
| 21.8 |
| 26.2 |
| 26.7 |

This polymorph is referred to as "polymorph C". The term "approximately" means in this context that there is an uncertainty in the measurements of the degrees 2-theta of ±0.2 (expressed in degrees 2-theta).

Preferably, the crystalline polymorph C as defined above is characterized by the x-ray powder diffraction pattern shown in FIG. 7.

The crystalline polymorph C as described above can also be characterized by its IR-spectrum. The present invention therefore also relates to a crystalline polymorph of the compound as defined above, which is characterized by an IR absorption spectrum having characteristic peaks expressed in cm⁻¹ at approximately 3497 cm⁻¹, 2748 cm⁻¹, 2655 cm⁻¹, 2239 cm⁻¹, 1883 cm⁻¹, 1667 cm⁻¹, 1641 cm⁻¹, 1554 cm⁻¹, 1377 cm⁻¹, 1361 cm⁻¹, 1333 cm⁻¹, 1288 cm⁻¹, 1269 cm⁻¹, 1161 cm⁻¹, 1088 cm⁻¹, 1070 cm⁻¹, 1047 cm⁻¹, 1024 cm⁻¹, 950 cm⁻¹, 914 cm⁻¹, 773 cm⁻¹, 714 cm⁻¹, 690 cm⁻¹, 650 cm⁻¹. The term "approximately" means in this context that the cm⁻¹ values can vary, e.g. by up to ±1 cm⁻¹. Preferably, the crystalline polymorph C as described above, is characterized by the IR absorption spectrum shown in FIG. 8.

Furthermore, the present invention relates to a crystalline polymorph of the compound as described above, which is characterized by an X-ray powder diffraction pattern having characteristic peaks expressed in degrees 2-theta at approximately

| degree 2-theta |
|---|
| 5.5 |
| 5.9 |
| 9.8 |
| 14.3 |
| 16.1 |
| 16.7 |
| 17.4 |
| 18.5 |
| 19.7 |
| 20.3 |
| 21.0 |
| 21.7 |
| 27.4 |

This polymorph is referred to as "polymorph D". The term "approximately" means in this context that there is an uncertainty in the measurements of the degrees 2-theta of ±0.2 (expressed in degrees 2-theta).

Preferably, the crystalline polymorph D as defined above is characterized by the x-ray powder diffraction pattern shown in FIG. 9.

The crystalline polymorph D as described above can also be characterized by its IR-spectrum. The present invention therefore also relates to a crystalline polymorph of the compound as defined above, which is characterized by an IR absorption spectrum having characteristic peaks expressed in $cm^{-1}$ at approximately 3418 $cm^{-1}$, 2661 $cm^{-1}$, 2454 $cm^{-1}$, 2249 $cm^{-1}$, 1901 $cm^{-1}$, 1666 $cm^{-1}$, 1639 $cm^{-1}$, 1552 $cm^{-1}$, 1430 $cm^{-1}$, 1378 $cm^{-1}$, 1354 $cm^{-1}$, 1329 $cm^{-1}$, 1315 $cm^{-1}$, 1287 $cm^{-1}$, 1235 $cm^{-1}$, 1197 $cm^{-1}$, 1160 $cm^{-1}$, 1090 $cm^{-1}$, 1072 $cm^{-1}$, 1042 $cm^{-1}$, 976 $cm^{-1}$, 949 $cm^{-1}$, 908 $cm^{-1}$, 866 $cm^{-1}$, 834 $cm^{-1}$, 784 $cm^{-1}$, 774 $cm^{-1}$, 721 $cm^{-1}$, 697 $cm^{-1}$, 652 $cm^{-1}$. The term "approximately" means in this context that the $cm^{-1}$ values can vary, e.g. by up to ±1 $cm^{-1}$. Preferably, the crystalline polymorph D as described above, is characterized by the IR absorption spectrum shown in FIG. 10

The degrees 2-theta values mentioned above refer to measurements with Cu Kα radiation, preferably with Cu Kα1 radiation, at 20-25° C.

Moreover, the invention relates especially to the compound (S)-1-{[2-(5-Methyl-2-phenyl-oxazol-4-yl)-ethylamino]-acetyl}-pyrrolidine-2-carbonitrile mesylate, wherein at least 70% are a crystalline polymorph as defined above, particularly wherein at least 90% are a crystalline polymorph as defined above, more particularly wherein at least 95% are a crystalline polymorph as defined above and even more particularly wherein at least 99% are a crystalline polymorph as defined above.

The invention further relates to a process for the manufacture of a compound or a crystalline polymorph as defined above, which process comprises reacting a compound of formula (II)

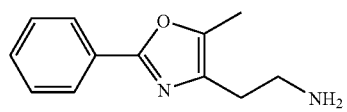

(II)

with a compound of formula (III)

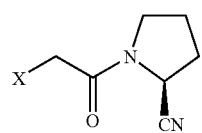

(III)

in the presence of Ca(OH)$_2$, wherein X is a leaving group.

The reaction of a compound of formula (II) with a compound of formula (III) can conveniently be carried out in a suitable solvent, such as e.g. DMF, DMA, THF, isopropanol or methylenechloride, preferably in DMF or DMA, more preferably in DMA. Preferably, the molar ratio of compound of formula (III) to compound of formula (II) is less than 1, e.g. 0.4 to 1, preferably 0.7 to 0.9, most preferably about 0.8. The reaction is conveniently carried out at a temperature of 15° C. to 40° C., preferably at 25° C. to 30° C. Possible leaving groups X in this context are e.g. halogen, triflate, mesylate or tosylate, preferably halogen, more preferably chlorine. The compound of formula (II) is preferably used in the form of its mesylate salt.

Compared to other reactions known in the art (e.g. from Journal of Medicinal Chemistry (2003), 46(13), 2774-2789; Journal of Medicinal Chemistry (2002), 45(12), 2362-2365; U.S. Pat. No. 6,011,155; US 2004106802), the reaction of the present invention as described above unexpectedly exhibits a largely improved yield and selectivity.

In a preferred embodiment, the present invention relates to a process as defined above, wherein the resulting compound (S)-1-{[2-(5-Methyl-2-phenyl-oxazol-4-yl)-ethylamino]-acetyl}-pyrrolidine-2-carbonitrile is subsequently converted to the mesylate salt. This conversion is preferably carried out with methane sulfonic acid in a suitable solvent such as e.g. methylenechloride, 2-butanone or THF, preferably in methylenechloride. The mesylate salt can then be obtained by subsequent crystallization, e.g. from THF or 2-butanone, preferably from 2-butanone.

Another preferred embodiment of the present invention relates to a process as defined above, wherein the resulting compound (S)-1-{[2-(5-Methyl-2-phenyl-oxazol-4-yl)-ethylamino]-acetyl}-pyrrolidine-2-carbonitrile mesylate is crystallized from isopropanol. Preferably, 5% to 10% (w/w), more preferably about 10% (w/w), of (S)-1-{[2-(5-Methyl-2-phenyl-oxazol-4-yl)-ethylamino]-acetyl}-pyrrolidine-2-carbonitrile are solved in isopropanol, preferably at a temperature of 40° C. to 70° C., more preferably 55° C. to 65° C., and crystallised by cooling. The isopropanol should be water free. This leads to polymorph A. Another preferred embodiment relates to a process as described above, comprising a crystallization from isopropanol, wherein seed crystals of polymorph D are added, in order to obtain polymorph D. Initial sample of polymorph D can be either be obtained in some minor cases by repeated crystallization from isopropanol or from wet grinding of polymorph B with isopropanol.

A further preferred embodiment of the present invention relates to a process as defined above, wherein the resulting compound (S)-1-{[2-(5-Methyl-2-phenyl-oxazol-4-yl)-ethylamino]-acetyl}-pyrrolidine-2-carbonitrile mesylate is crystallized from a mixture of isopropanol and water. Preferably, 5% to 10% (w/w), more preferably about 10% (w/w), of (S)-1-{[2-(5-Methyl-2-phenyl-oxazol-4-yl)-ethylamino]-acetyl}-pyrrolidine-2-carbonitrile are solved in a mixture of isopropanol and water, preferably at a temperature of 40° C. to 70° C., more preferably 55° C. to 65° C., and crystallized by cooling. The isopropanol should be mixed with 2% to 5% (w/w), preferably with 2.5% to 3.5% (w/w) of water. This leads to polymorph B.

Still another preferred embodiment of the present invention relates to a process as defined above, wherein the resulting compound (S)-1-{[2-(5-Methyl-2-phenyl-oxazol-4-yl)-ethylamino]-acetyl}-pyrrolidine-2-carbonitrile mesylate is crystallized from 2-butanone. Crystallization from 2-butanone can be carried out in the presence of a co-solvent such as e.g. DMA or DMF. Crystallization can also be carried out by digestion in 2-butanone. The solvents should preferably be water free or have a water content of less than 0.5% (w/w). This leads to polymorph C.

A preferred embodiment of the present invention is related to a process as defined above, wherein the compound of formula (III) is obtained by reacting a compound of formula (IV)

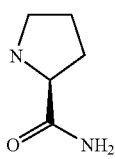

with ClCH₂COCl and subsequent dehydratisation to obtain said compound of formula (III)

The reaction of a compound of formula (IV) with ClCH₂COCl can be carried out in a solvent such as e.g. DMA, DMF, THF, dioxane, ethylacetate or methylenechloride, preferably in methylenechloride, and in the presence of a base such as e.g. ET₃N,N-ethyldiisopropylamine or imidazol, preferably ET₃N. The reaction can be carried out at a suitable temperature, e.g. in the range of −80° C. to −30° C., preferably at −50° C. to −40° C. The subsequent dehydratisation can be carried out in a solvent such as e.g. DMA, DMF, THF, dioxane, ethylacetate or methylenechloride, preferably in methylenechloride or DMF or a mixture of methylenechloride and DMF, with a dehydrating agent such as e.g. cyanurchlorid, chlormethyliminiumchlorid, SOCl₂ or POCl₃, preferably chlormethyliminiumchlorid, SOCl₂ or POCl₃, more preferably POCl₃. The reaction can be carried out at a suitable temperature, e.g. in the range of at −20° C. to 40° C., preferably at −5° C. to 25° C.

Compared to other reactions known in the art (e.g. from Journal of Medicinal Chemistry, 46(13), 2774-2789, 2003; Journal of Medicinal Chemistry, 45(12), 2362-2365, 2002; U.S. Pat. No. 6,011,155; US 2004/106802), the reaction of the present invention as described above unexpectedly exhibits a largely improved yield and selectivity. The present invention also relates to a process for the preparation of a compound of formula (III) as described above.

Another preferred embodiment of the present invention is related to a process as defined above, wherein the compound of formula (II) is obtained by hydrogenating a compound of formula (V)

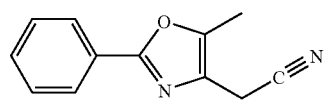

The hydrogenation of the compound of formula (V) can conveniently be carried out in a solvent such as e.g. methanol, ethanol, isopropanol, benzene, toluene, pentan/octan, THF, dioxan, or pyridin, preferably in ethanol. The hydrogenation is carried out in the presence of a catalyst such as e.g. Raney Nickel, Raney Cobalt, nickel on carrier or cobalt on carrier, preferably Raney Cobalt. Hydrogen can be used at a suitable pressure, e.g. at 1 to 100 bar, preferably 1 to 60 bar, more preferably 3 to 15 bar. The temperature is conveniently chosen between room temperature and 100° C., preferably between room temperature and 80° C., more preferably between 55° C. and 75° C. Preferably, the hydrogenation is carried out in the presence of an additive such as e.g. NH₃, ethanolamin or sodium formiate, preferably NH₃, when Raney Nickel is used as a catalyst. Sodium formiate can also be used as an additive, when Raney Cobalt is used as a catalyst. The starting material of formula (V) is commercially available and has been described in WO 03/040114.

Compared to other reactions known in the art (e.g. from WO 03/037327; WO 03/018553;), the reaction of the present invention as described above unexpectedly exhibits a largely improved yield and selectivity. The present invention also relates to a process for the preparation of a compound of formula (II) as described above.

Another preferred embodiment of the present invention relates to a process as defined above, wherein the compound of formula (II) is obtained by reacting a compound of formula (VI)

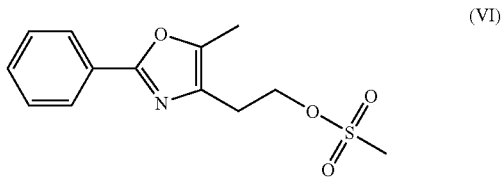

with NH₃.

The reaction of a compound of formula (VI) with NH₃ can conveniently be carried out in a solvent, such as e.g. aliphatic C₁₋₄-alcohols, toluene or THF, preferably in methanol. Preferably, the compound of formula (VI) and NH₃ are used at a weight ration of 1/1.2 to 1/2.4, preferably 1/1.8 to 1/2.2, most preferably about ½. The reaction can preferably be carried out at a temperature of 50° C. to 90° C., more preferably at a temperature in the range of 70° C. to 80° C. The starting material of formula (VI) is known in the art and can be prepared by methods known in the art (e.g. from Journal of Labelled Compounds & Radiopharmaceuticals, 46(7), 605-611; 2003; WO 2001/079202; WO 99/50267). Preferably, the compound of formula (II) is obtained as mesylate salt. Compared to methods known in the art, the above described reaction unexpectedly exhibits a largely improved yield and selectivity.

In the reactions as defined above, the compound of formula (II) is preferably in the form of the mesylate salt. The present invention also relates to the compound 2-(5-Methyl-2-phenyl-oxazol-4-yl)-ethylammonium mesylate, which is an intermediate compound in the reactions as defined above. The present invention also relates to a process for the preparation of a compound of formula (II) as described above.

Furthermore, the invention relates to a compound or crystalline polymorph as defined above, when manufactured by a process as described above.

As described above, the compounds and/or polymorphs of the present invention can be used as medicaments for the treatment and/or prophylaxis of diseases which are associated with DPP-IV such as diabetes, particularly non-insulin dependent diabetes mellitus, impaired glucose tolerance, bowl disease, colitis ulcerosa, morbus crohn, obesity, and/or metabolic syndrome, preferably non-insulin dependent diabetes mellitus and/or impaired glucose tolerance. Furthermore, the compounds and/or polymorphs of the present invention can be used as diuretic agents or for the treatment and/or prophylaxis of hypertension.

The invention therefore also relates to pharmaceutical compositions comprising a compound or crystalline polymorph as defined above and a pharmaceutically acceptable carrier and/or adjuvant.

Further, the invention relates to a compound or crystalline polymorph as defined above for use as therapeutic active substance, particularly as therapeutic active substance for the treatment and/or prophylaxis of diseases which are associated with DPP-IV such as diabetes, particularly non-insulin dependent diabetes mellitus, impaired glucose tolerance, bowl disease, colitis ulcerosa, morbus crohn, obesity, and/or metabolic syndrome, preferably for use as therapeutic active substances for the treatment and/or prophylaxis of non-insulin dependent diabetes mellitus and/or impaired glucose tolerance. The invention relates furthermore to a compound or crystalline polymorph as defined above for use as diuretic agents or for use as therapeutic active substance for the treatment and/or prophylaxis of hypertension.

In another embodiment, the invention relates to a method for the treatment and/or prophylaxis of diseases which are associated with DPP-IV such as diabetes, particularly non-insulin dependent diabetes mellitus, impaired glucose tolerance, bowl disease, colitis ulcerosa, morbus crohn, obesity, and/or metabolic syndrome, preferably for the treatment and/or prophylaxis of non-insulin dependent diabetes mellitus and/or impaired glucose tolerance, which method comprises administering a compound or crystalline polymorph as defined above to a human being or animal. The invention relates furthermore to a method for the treatment and/or prophylaxis as defined above, wherein the disease is hypertension or wherein a diuretic agent has a beneficial effect.

The invention further relates to the use of a compound or crystalline polymorph as defined above for the treatment and/or prophylaxis of diseases which are associated with DPP-IV such as diabetes, particularly non-insulin dependent diabetes mellitus, impaired glucose tolerance, bowl disease, colitis ulcerosa, morbus crohn, obesity, and/or metabolic syndrome, preferably for the treatment and/or prophylaxis of non-insulin dependent diabetes mellitus and/or impaired glucose tolerance. The invention relates furthermore to the use as defined above, wherein the disease is hypertension or to the use as diuretic agent.

In addition, the invention relates to the use of a compound or crystalline polymorph as defined above for the preparation of medicaments for the treatment and/or prophylaxis of diseases which are associated with DPP-IV such as diabetes, particularly non-insulin dependent diabetes mellitus, impaired glucose tolerance, bowl disease, colitis ulcerosa, morbus crohn, obesity, and/or metabolic syndrome, preferably for the treatment and/or prophylaxis of non-insulin dependent diabetes mellitus and/or impaired glucose tolerance. Such medicaments comprise a compound as defined above. The invention relates furthermore to the use as defined above, wherein the disease is hypertension or the use for the preparation of diuretic agents.

In context with the methods and uses defined above, the following diseases relate to a preferred embodiment: diabetes, particularly non-insulin dependent diabetes mellitus, impaired glucose tolerance, obesity, and/or metabolic syndrome, preferably non-insulin dependent diabetes mellitus and/or impaired glucose tolerance.

In the compositions, uses and methods as described above, the compound (S)-1-{[2-(5-Methyl-2-phenyl-oxazol-4-yl)-ethylamino]-acetyl}-pyrrolidine-2-carbonitrile mesylate, the polymorphs as described above, or the compound (S)-1-{[2-(5-Methyl-2-phenyl-oxazol-4-yl)-ethylamino]-acetyl}-pyrrolidine-2-carbonitrile mesylate wherein at least 70% are a crystalline polymorph as defined above, particularly wherein at least 90% are a crystalline polymorph as defined above, more particularly wherein at least 95% are a crystalline polymorph as defined above and even more particularly wherein at least 99% are a crystalline polymorph as defined above, can be used.

The following tests were carried out in order to determine the activity of the compounds and crystalline polymorphs as described above.

Activity of DPP-IV inhibitors are tested with natural human DPP-IV derived from a human plasma pool or with recombinant human DPP-IV. Human citrate plasma from different donors is pooled, filtered through a 0.2 micron membrane under sterile conditions and aliquots of 1 mL are shock frozen and stored at −120° C. until used. In the colorimetric DPP-IV assay 5 to 10 μL human plasma and in the fluorometric assay 1.0 μL of human plasma in a total assay volume of 100 μL is used as an enzyme source. The cDNA of the human DPP-IV sequence of amino acid 31- to 766, restricted for the N-terminus and the transmembrane domain, is cloned into pichia pastoris. Human DPP-IV is expressed and purified from the culture medium using conventional column chromatography including size exclusion and anion and cation chromatography. The purity of the final enzyme preparation of Coomassie blue SDS-PAGE is >95%. In the calorimetric DPP-IV assay 20 ng rec.-h DPP-IV and in the fluorometric assay 2 ng rec-h DPP-IV in a total assay volume of 100 μL is used as an enzyme source.

In the fluorogenic assay Ala-Pro-7-amido-4-trifluoromethylcoumarin (Calbiochem No 125510) is used as a substrate. A 20 mM stock solution in 10% $DMF/H_2O$ is stored at −20° C. until use. In IC50 determinations a final substrate concentration of 50 μM is used. In assays to determine kinetic parameters as Km, Vmax, Ki, the substrate concentration is varied between 10 μM and 500 μM.

In the calorimetric assay H-Ala-Pro-pNA.HCl (Bachem L-1115) is used as a substrate. A 10 mM stock solution in 10% $MeOH/H_2O$ is stored at −20° C. until use. In IC50 determinations a final substrate concentration of 200 μM is used. In assays to determine kinetic parameters as Km, Vmax, Ki, the substrate concentration is varied between 100 μM and 2000 μM. Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression. The absorption of pNA liberated from the calorimetric substrate is detected in a Packard SpectraCount at 405 nM continuously every 2 minutes for 30 to 120 minutes. Initial rate constants are calculated by best fit linear regression.

DPP-IV activity assays are performed in 96 well plates at 37° C. in a total assay volume of 100 μl. The assay buffer consists of 50 mM Tris/HCl pH 7.8 containing 0.1 mg/mL BSA and 100 mM NaCl. Test compounds are solved in 100% DMSO, diluted to the desired concentration in 10% $DMSO/H_2O$. The final DMSO concentration in the assay is 1% (v/v). At this concentration enzyme inactivation by DMSO is <5%. Compounds are with (10 minutes at 37° C.) and without preincubation with the enzyme. Enzyme reactions are started with substrate application followed by immediate mixing.

IC50 determinations of test compounds are calculated by non-linear best fit regression of the DPP-IV inhibition of at least 5 different compound concentrations. Kinetic parameters of the enzyme reaction are calculated at least 5 different substrate concentrations and at least 5 different test compound concentrations.

The compounds and crystalline polymorphs of the present invention exhibit IC50 values in the range of 10 nM to 500 nM, more preferably of 50-100 nM.

| Compound | IC$_{50}$ [nM] | Ki [nM] |
|---|---|---|
| (S)-1-{[2-(5-Methyl-2-phenyl-oxazol-4-yl)-ethylamino]-acetyl}-pyrrolidine-2-carbonitrile mesylate | 75 | 80 |

The compounds and polymorphs of the present invention can be used as medicament, e.g. in the form of pharmaceutical preparations for enteral, parenteral or topical administration. It can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils.

The production of the pharmaceutical preparations can be effected in a manner which will be familiar to any person skilled in the art by bringing the described polymorph, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds and polymorphs of the present invention can vary within wide limits depending on the disease to be controlled, the age and the individual condition of the patient and the mode of administration, and will, of course, be fitted to the individual requirements in each particular case. For adult patients a daily dosage of about 50 to 2000 mg, especially about 200 to 1000 mg, comes into consideration. Depending on severity of the disease and the precise pharmacokinetic profile the compounds and polymorphs of the present invention could be administered with one or several daily dosage units, e.g. in 1 to 3 dosage units.

The pharmaceutical preparations conveniently contain about 50 to 1000 mg, preferably 200 to 500 mg, of a compound and/or polymorph of the present invention.

The following examples serve to illustrate the present invention in more detail. They are, however, not intended to limit its scope in any manner. The compound (S)-1-{[2-(5-Methyl-2-phenyl-oxazol-4-yl)-ethylamino]-acetyl}pyrrolidine-2-carbonitrile can be obtained according to the methods disclosed in WO 03/037327 or by the methods given above or in the examples. The compounds and polymorphs according to the present invention can be manufactured by the methods given above, by the methods given in the examples or by analogous methods. Starting materials are either commercially available or can be prepared by methods analogous to the methods given above or in the examples or by methods known in the art.

EXAMPLES

X-Ray Powder Diffraction

The X-ray powder diffraction patterns were recorded with a STOE Stadi P X-ray diffractometer in transmission mode (Cu K$\alpha$1 radiation, Ge-monochromator, position sensitive detector (PSD), angular range 3° to 42° 2Theta, steps of 0.5° 2Theta, measuring time 40 seconds per step). The samples were prepared and analyzed without further processing (e.g. grinding or sieving) of the substance. For obtaining the X-ray powder diffraction pattern of the dried sample, powder in an unsealed glass capillary was stored in a hot-stage device attached to the STOE Stadi P diffractometer at 80° C. for 24 hours. Then the capillary was immediately sealed with epoxy resin and measured at ambient temperature (20-25° C.).

IR-Spectroscopy

The IR-spectra of the samples were recorded as film of a Nujol suspension consisting of approx. 5 mg of sample and few Nujol between two sodium chloride plates, with an FT-IR spectrometer in transmittance. The Spectrometer is a Nicolet 20SXB or equivalent (resolution 2 cm$^{-1}$, 32 or more coadded scans, MCT detector).

Growth and X-Ray Structure Analysis of Single Crystals

To obtain single crystals for structure analysis, 200 mg of (S)-1-{[2-(5-Methyl-2-phenyl-oxazol-4-yl)-ethylamino]-acetyl}-pyrrolidine-2-carbonitrile mesylate were dissolved in a mixture of 3.88 mL 2-propanol and 120 μL water at 50° C. The solution was transferred via a 0.2 μm filter into 10 mL glass vial. The vial was then closed and was put into a 1 L water bath with at temperature of 45° C. The system was allowed to reach ambient temperature passively. After 2 days single crystals were harvested for x-ray data collection. The crystals were mounted in glass capillaries and sealed with epoxy resin at the normal ambient conditions in the laboratory. For obtaining the structure of the dried crystal, crystals in an unsealed glass capillary were stored in a vacuum dryer at 5 mbar and 40° C. for 12 days. Then the capillary was removed from the incubator and sealed immediately with epoxy resin.

The capillary containing a single crystal was mounted on a goniometer and data were collected on a single crystal X-ray Diffractometer and processed with standard data reduction software. In this case Mo-radiation of 0.71 Å wavelength and an Imaging Plate Diffraction System from STOE (Darmstadt) was used for data collection and data was processed with STOE IPDS-software. The crystal structure was solved and refined with standard crystallographic software. In this case the program ShelXTL-NT V6.1 from Bruker AXS (Karlsruhe) was used.

Example 1

A 500 mL double jacketed glass reactor equipped with a mechanical stirrer, a Pt-100 thermometer, a reflux condenser, a dropping funnel and a nitrogen inlet was charged with 77.8 mL (1007 mmol) of dimethylformamide and 35 mL of methylenechloride. The solution was cooled and treated with phosphorous oxychloride (75.4 g, 482 mmol) within maximal 60 min at 0° C. to 7° C. The dropping funnel was rinsed with 5 mL of methylenechloride. The clear solution was stirred at 0° C. to 5° C. for 60 to 120 min. This solution was then transferred into a 250 mL dropping funnel. The reactor was rinsed with 10 mL of methylenechloride.

A 1000 mL double jacketed glass reactor equipped with a mechanical stirrer, a Pt-100 thermometer, a reflux condenser, a dropping funnel and a nitrogen inlet was charged with 50.0 g (483 mmol) of L-Prolinamide and 230 mL of methylenechloride. The suspension was stirred and treated with 51.2 g (504 mmol) of triethylamine and cooled to −40° C. to −50° C. and a solution of 58.0 g (508 mmol) of chloroacetylchloride in 50 mL of methylenechloride was added within 60 to 90 min. The dropping funnel was rinsed with 5 mL of methylenechloride. The suspension was warmed up to −5° C. to 0° C. within 1 h. The resulting (S)-1-(2-Chloro-acetyl)-pyrrolidine-2-carboxylic acid amide was dehydrated while adding the solution of the Vilsmeier-Reagent from the first reaction within 1 to 15 min at −5° C. to 5° C. The dropping funnel was rinsed with 5 mL of methylenechloride and the resulting mixture was stirred for about 1 h at −5° C. to 5° C. The reaction mixture was then poured onto 175 mL of water within 10 to 30 min and at a temperature of 5° C. to 20° C. The reactor was rinsed with 5 mL of methylenechloride. The mixture was stirred at RT for at least 30 min. The phases were separated and the aqueous phase was twice extracted with a total of 170 mL of methylenechloride. The organic phases were unified and washed with 88 mL of water. The resulting organic phase was concentrated under vacuum (500 mbar to 50 mbar) at 20° C. to 50° C. The resulting oil was treated within 10 to 30 min with 325 mL of isopropanol and heated to 45° C. Subsequently, the solution was again cooled to 25° C. to 30° C. within 20 min and inoculated where after the product started to precipitate. The suspension was stirred for 1 h at this temperature and then cooled down to −15° C. to −20° C. within 4 h. The crystallization was completed by the addition of 85 ml of n-heptane and the mixture was kept stirring for another 2 h. The precipitate was filtered with suction, the filter cake was washed with cold (−10° C. to 20° C.) n-heptane (140 mL) and dried to constant weight (50° C., 50 mbar, 3 h) to afford 62.6 g of (S)-1-(2-chloroacetyl)-pyrrolidine-2-carbonitrile. (Yield: 83%, assay: 100% (m/m) based on HPLC). The HPLC analysis was performed with an external standard of pure (S)-1-(2-chloroacetyl)-pyrrolidine-2-carbonitrile. Conditions for HPLC: Column Atlantis™ dC18 Waters, 3.9× 150 mm, 3 µm, UV detection 205 nm, solutions for gradient: water (A), acetonitrile (B), pH 4.9 buffer KH2PO4 (C); flow 1.2 mL/min, 40° C.

| Gradient: | | | | |
|---|---|---|---|---|
| Min | A | B | C | |
| 0 | 90 | 5 | 5 | isocratic |
| 15 | 25 | 70 | 5 | linear gradient |
| 5 | 90 | 5 | 5 | post time |

Retention Times:

(S)-1-(2-Chloro-acetyl)-pyrrolidine-2-carboxylic acid amide: approx. 3.26 min

N-Formyl (S)-1-(2-Chloro-acetyl)-pyrrolidine-2-carboxylic acid amide: approx. 4.68 min (S)-1-(2-Chloroacetyl)-pyrrolidine-2-carbonitrile: approx. 5.56 min

Example 2

This example was run in an analogous manner as example 1 but starting from 20.0 g (175.2 mmol) of L-Prolinamide (1), 20.5 g (201 mmol) of triethylamine, 23.2 g (203 mmol) of chloroactylchloride and totally 112 mL of methylenechloride. The resulting (S)-1-(2-Chloro-acetyl)-pyrrolidine-2-carboxylic acid amide was dehydrated while adding a solution of the Vilsmeier-Reagent at RT that was prepared from 33.8 mL (438 mmol) of DMF, 20 mL of methylenechloride and 25.3 g (201 mmol) of thionylchloride. The resulting mixture was stirred for 90 min, then quenched with water and extracted in an analogous manner as example 1. Crystallization from Isopropanol/n-heptane and drying afforded 24.7 g of (S)-1-(2-Chloroacetyl)-pyrrolidine-2-carbonitrile. (Yield: 82%, assay: 99.9% (m/m) based on HPLC).

Example 3

This example was run in an analogous manner as example 1 but starting from 20.0 g (175.2 mmol) of L-Prolinamide (1), 22.0 g (217 mmol) of triethylamine, 24.7 g (218 mmol) of Chloroactylchloride and totally 112 mL of methylenechloride. The resulting (S)-1-(2-Chloro-acetyl)-pyrrolidine-2-carboxylic acid amide was treated at 2° C. to 5° C. with a solution of 26.1 g (198 mmol) of chloromethylen-dimethyliminium chloride in 14 mL (438 mmol) of DMF. The resulting mixture was stirred at least for 35 min at 1.5° C. to 5° C. showing a complete turnover (HPLC). According to HPLC, the reaction profile corresponded with example 1.

Example 4

This example was run in an analogous manner as example 1 but starting from 20.0 g (175.2 mmol) of L-Prolinamide (1), 17.6 g (173.5 mmol) of triethylamine, 22.7 g (199.4 mmol) of Chloroactylchloride and totally 152 mL of methylenechloride. The resulting (S)-1-(2-Chloro-acetyl)-pyrrolidine-2-carboxylic acid amide was treated with 20 mL of DMF and 12.7 g (67.5 mmol) of cyanurchloride at 20° C. The resulting mixture was heated to 35° C., stirred for 2 h at this temperature and treated with 2.6 mL of water. The suspension was stirred for 1 h at RT and filtered with suction. The filter cake was washed with 20 mL of methylenechloride and the filtrate was treated with 100 mL of water. The layers were separated and the aqueous phase was twice washed with a total of 68 mL of methylenechloride. The organic layers were unified and concentrated under vacuum at a jacket temperature of 40° C.

(400 mbar to 28 mbar). The remaining oil was treated with 130 mL of Isopropanol and inoculated at 30° C. The suspension was cooled to −22° C. within 4 h, stirred over night at this temperature and treated with 34 mL of n-heptane. The precipitate was filtered with suction, the filter cake was washed with 112 mL of a cold (−10° C. to 20° C.) mixture of n-heptane/2-propanol (8:2 (v/v)) and dried to constant weight (50° C., 50 mbar, 3 h) to afford 24.0 g of (S)-1-(2-Chloroacetyl)-pyrrolidine-2-carbonitrile. (Yield: 80%, assay: 100% (m/m) based on HPLC).

Example 5

A suspension of 3.0 g of commercially available Raney Cobalt (Johnson Matthey 8B0022, wet, ca. 50 weight %) in 20 mL of ethanol was treated for 3 min with 522 mg (7.60 mmol) of sodium formate. This suspension was transferred together with 60 g (302 mmol) of (5-Methyl-2-phenyl-oxazol-4-yl)-acetonitrile with aid of 280 mL of ethanol to a 1.5 L stainless steel autoclave, which was sealed and charged with 9 bar of hydrogen. The hydrogenation was carried out under vigorous stirring for 4 h at a temperature of 70° C. and 10 bar (4 MPa) of hydrogen. After this time the autoclave was cooled to room temperature, the pressure released and the reaction mixture filtered. Addition to the filtrate under argon of 21 mL (324 mmol) of trifluoromethane sulphonic acid leads to the precipitation as 82 g of 2-(5-Methyl-2-phenyl-oxazol-4-yl)-ethylamine as its mesylate salt as a white crystalline material with melting point of 230-231° C. (dec). HPLC analysis of the hydrogenation mixture showed a selectivity to the desired product of 96% (HPLC area %). HPLC analysis with internal standard of the crystalline mesylate salt showed a purity of 99.5%. Conditions of HPLC analysis: Column XTerra RP8 Waters, 4.6×150 mm, 3.5 μm; UV detector 205 nm; solutions for gradient water/acetonitrile 95:5 (A), acetonitrile (B), pH 3 buffer $Bu_4NHSO_4$ (C); flow 1 mL/min, 40° C.

| | Gradient: | | |
|---|---|---|---|
| Min | A | B | C |
| 0 | 80 | 10 | 10 |
| 3 | 80 | 10 | 10 |
| 20 | 10 | 80 | 10 |
| 24 | 10 | 80 | 80 |
| 25 | 80 | 10 | 10 |

Retention Times:

(5-Methyl-2-phenyl-oxazol-4-yl)-acetonitrile: approx. 13.76 min 2-(5-Methyl-2-phenyl-oxazol-4-yl)-ethylamine: approx. 3.13 min Bis-[2-(5-methyl-2-phenyl-oxazol-4-yl)-ethyl]-amine: approx. 12.48 min Tris-[2-(5-methyl-2-phenyl-oxazol-4-yl)-ethyl]-amine: approx. 15.58 min

Example 6

This example was run in an analogous manner as example 5 but using 6.0 g of wet Raney Cobalt catalyst (same brand as Example 5) and without addition of sodium formate as modifier. After 14 h the autoclave was opened and the reaction mixture worked-up as in example 1 to afford after crystallization 80.8 g of 2-(5-Methyl-2-phenyl-oxazol-4-yl)-ethylamine as its mesylate salt as a white crystalline material of 99.5% (HPLC area %) purity.

Example 7

6.00 g (30 mmol) of (5-Methyl-2-phenyl-oxazol-4-yl)-acetonitrile were hydrogenated in the presence of 0.60 g of wet Raney Cobalt catalyst (Grace Davison Catalysts, Worms, Germany, Type Nr. 2700) in 54 mL of methanol in a 185 mL stainless steel autoclave under 9 bar of hydrogen pressure at 80° C. for 4 h. Removal of the catalyst by filtration, evaporation of the solvents and drying (45° C./10 mbar/2 h) afforded 6.15 g of 2-(5-Methyl-2-phenyl-oxazol-4-yl)-ethylamine with a purity of 87.7% (HPLC area %).

Example 8

6.00 g (30 mmol) of (5-Methyl-2-phenyl-oxazol-4-yl)-acetonitrile were hydrogenated in the presence of 0.60 g of wet Raney Cobalt catalyst (Blackwell-Catalloy, Type Nr. 1708042) in 54 mL of ethanol in a 185 mL stainless steel autoclave under 9 bar of hydrogen pressure at 70° C. for 3 h. Removal of the catalyst by filtration, evaporation of the solvents and work-up as in example 1 afforded 7.63 g of 2-(5-Methyl-2-phenyl-oxazol-4-yl)-ethylamine as its mesylate salt with a purity of 100% (HPLC area %).

Example 9

This example was run in an analogous manner as example 5 but using 6.00 g (30 mmol) of (5-Methyl-2-phenyl-oxazol-4-yl)-acetonitrile in the presence of 0.60 g of wet Raney Cobalt catalyst (Johnson Matthey 8B0022, wet, ca. 50 weight %) in the presence of 50 mg of sodium acetate as modifier in a 185 mL autoclave at 70° C. under 9 bar of hydrogen pressure for 1.5 h. Removal of the catalyst by filtration, evaporation of the solvents and drying (50° C./10 mbar/2 h) afforded 6.27 g of 2-(5-Methyl-2-phenyl-oxazol-4-yl)-ethylamine with a purity of 89.3% (HPLC area %).

Example 10

This example was run in an analogous manner as example 5 but using 6.00 g (30 mmol) of (5-Methyl-2-phenyl-oxazol-4-yl)-acetonitrile in the presence of 0.60 g of wet Raney Cobalt catalyst (Johnson Matthey 8B0022, wet, ca. 50 weight %) in the presence of 40 μL of ethanolamine as modifier in a 185 mL autoclave at 70° C. under 9 bar of hydrogen pressure for 1.5 h. Removal of the catalyst by filtration, evaporation of the solvents and drying (50° C./10 mbar/2 h) afforded 6.21 g of 2-(5-Methyl-2-phenyl-oxazol-4-yl)-ethylamine with a purity of 90.3% (HPLC area %).

Example 11

This example was run in an analogous manner as example 5 but using 6.0 g of wet Raney Nickel catalyst (Engelhard Actimet MD) and with addition of 1.21 mol of ammonia (as 200 mL of a ca 13% ethanolic solution) as modifier, the total volume of solvent being 540 mL. After 4 h the autoclave was opened and the reaction mixture worked-up as in example 5 to afford after crystallization 80.0 g of 2-(5-Methyl-2-phenyl-oxazol-4-yl)-ethylamine as its mesylate salt as a white crystalline material of 100% (HPLC area %) purity.

Example 12

This example was run in an analogous manner as example 11 but using methanol as the solvent. Work-up afforded 86.1 g of 2-(5-Methyl-2-phenyl-oxazol-4-yl)-ethylamine as its mesylate salt as a white crystalline material of 98.1% (HPLC area %) purity.

Example 13

This example was run in an analogous manner as example 11 but using ethanolamine (7.3 mL) as the modifier in 47 mL of ethanol as solvent under 10 bar of hydrogen pressure for 3 h. Removal of the catalyst by filtration, evaporation of the solvents and drying (50° C./10 mbar/2 h) showed complete conversion and afforded 13.28 g of 2-(5-Methyl-2-phenyl-oxazol-4-yl)-ethyl-amine as a mixture with ethanolamine with 67% (HPLC area %) content of the desired product.

Example 14

A 1500 mL double jacketed stainless steel autoclave equipped with a mechanical stirring bar and a Pt-100 thermometer was charged under nitrogen with 100 g (355 mmol) of methanesulfonic acid 2-(5-methyl-2-phenyl-oxazol-4-yl)-ethyl ester and 900 mL of methanol. The autoclave was closed and ammonia (200 g, 11.74 mol) was transferred into the suspension at −20° C. to 20° C. while stirring and cooling. The mixture was then heated to 75° C.-80° C. and the pressure rose to 10 bar. The mixture was stirred for 2-3 h at this temperature and then cooled down to 20° C. The pressure was relieved and the clear solution was transferred with the aid of 100 mL of methanol to a 1000 mL double jacketed glass reactor equipped with a mechanical stirrer, a Pt-100 thermometer, a reflux condenser, a dropping funnel and a nitrogen inlet. The solvent was completely removed by distillation under vacuum. The resulting suspension was twice treated with 500 mL of methylenechloride that was subsequently completely removed by distillation under normal pressure. The residue was again treated with 500 mL of methylenechloride and the resulting suspension was cooled to 0° C. within 1 h and stirred for another 2 h at this temperature. The precipitate was filtered with suction, the filter cake was washed with 200 mL of methylenechloride and dried under vacuum (50° C., 50 mbar) to afford about 85.8 g (yield 78%, 96% (m/m) purity based on HPLC assay) of 2-(5-Methyl-2-phenyl-oxazol-4-yl)-ethylammonium mesylate as a colorless solid. The HPLC analysis was performed with an external standard of pure 2-(5-methyl-2-phenyl-oxazol-4-yl)-ethylammonium mesylate. Conditions for HPLC: Column XTerra RP8 Waters, 4.6×150 mm, 3.5 μm; UV detector 205 nm; solutions for gradient: water (A), acetonitrile (B), pH 6.5 buffer KH2PO4/K2HPO4 (C); flow 1.2 mL/min, 40° C.

Retention Times:

Methanesulfonic acid 2-(5-methyl-2-phenyl-oxazol-4-yl)-ethyl ester: approx. 15.2 min 2-(5-Methyl-2-phenyl-oxazol-4-yl)-ethylamine: approx. 7.97 min Bis-[2-(5-methyl-2-phenyl-oxazol-4-yl)-ethyl]-amine: approx. 18.15 min Tris-[2-(5-methyl-2-phenyl-oxazol-4-yl)-ethyl]-amine: approx. 22.08 min

Example 15

A 1000 mL double jacketed glass reactor equipped with a mechanical stirrer, a Pt-100 thermometer, a reflux condenser, a dropping funnel and a nitrogen inlet was charged with 60 g (199.5 mmol) of 2-(5-Methyl-2-phenyl-oxazol-4-yl)-ethylammonium mesylate, 15.4 g (199.4 mmol) of calciumhydroxyde and 350 mL of DMA. The resulting suspension was heated to 25° C. to 30° C. and stirred for 15 to 60 min at this temperature. A solution of 27.5 g (159.6 mmol) of (S)-1-(2-chloroacetyl)-pyrrolidine-2-carbonitrile in 54.4 g of DMA was added-within 15 to 30 min and the dropping funnel was rinsed with 10 mL of DMA. The mixture was heated to 25° C. to 30° C. and stirred for 1 to 2 h at this temperature. The reaction mixture was cooled to RT and treated with 400 mL of methylenechloride and 300 mL of Water. The pH of the resulting mixture was set with 1M methanesulfonic acid (ca. 80 mL) to 7.8. The mixture was then stirred for about 30 min at RT. The phases were separated and the aqueous phase was extracted with 200 mL of methylenechloride. The combined organic layers were twice extracted with totally 400 mL of aqueous 1% NaCl solution. The organic phase was cooled to 5° C. to 15° C. and methanesulfonic acid (13.6 g, 139.7 mmol) was added within 5 min. Methylenechloride was completely removed first under normal pressure, then under vacuum (500-50 mbar) at a jacket temperature of maximal 55° C. While adding 700 mL of 2-butanone at 38° C. to 42° C. within 40 to 60 min to the resulting residue, the product precipitated and subsequently, 180 to 220 mL of 2-butanone were distilled off under vacuum (170 to 250 mbar). The resulting suspension was cooled to 10° C. within 3-4 h and stirred at this temperature for at least 2 h. The precipitate was filtered with suction, the filter cake was washed with 100 mL of cold 2-butanone (−10° C.) and dried under vacuum (50° C., 50 mbar) to afford about 61.3 g (yield 85% starting from of (S)-1-(2-chloroacetyl)-pyrrolidine-2-carbonitrile, 94.9% (m/m) purity based on HPLC assay) of (S)-1-{[2-(5-methyl-2-phenyl-oxazol-4-yl)-ethylamino]-acetyl}-pyrrolidine-2-carbonitrile mesylate as a colorless solid. The HPLC analysis was performed with an external standard of pure (S)-1-{[2-(5-methyl-2-phenyl-oxazol-4-yl)-ethylamino]-acetyl}-pyrrolidine-2-carbonitrile mesylate. Conditions for HPLC: Column XTerra RP8 Waters, 4.6×150 mm, 3.5 μm; UV detector 220 nm; solutions for gradient: water (A), acetonitrile (B), pH 6.5 buffer KH2PO4/K2HPO4 (C); flow 1.2 mL/min, 40° C.

| | Gradient: | | | |
|---|---|---|---|---|
| Min | A | B | C | |
| 0 | 80 | 10 | 10 | |
| 13 | 50 | 40 | 10 | linear gradient |
| 20 | 10 | 80 | 10 | linear gradient |
| 25 | 10 | 80 | 10 | isocratic |
| 5 | 80 | 10 | 10 | post-time |

| | Gradient: | | | |
|---|---|---|---|---|
| Min | A | B | C | |
| 0 | 70 | 20 | 10 | isocratic |
| 20 | 20 | 70 | 10 | linear gradient |
| 5 | 70 | 20 | 10 | post-time |

Retention Times:

(S)-1-(2-Chloroacetyl)-pyrrolidine-2-carbonitrile: approx. 2.56 min 2-(5-Methyl-2-phenyl-oxazol-4-yl)-ethylamine: approx. 3.94 min (S)-1-{[2-(5-Methyl-2-phenyl-oxazol-4-yl)-ethylamino]-acetyl}-pyrrolidine-2-carbonitrile: approx. 7.94 min Dialkylated product: approx. 10.95 min

Example 16

This example was run in an analogous manner as example 15 but starting from 30.0 g (100.6 mmol) of 2-(5-Methyl-2-phenyl-oxazol-4-yl)-ethylammonium mesylate in DMF. Thus a 1000 mL double jacketed glass reactor equipped with a mechanical stirrer, a Pt-100 thermometer, a reflux condenser, a dropping funnel and a nitrogen inlet was charged with 30 g (100.6 mmol) of 2-(5-Methyl-2-phenyl-oxazol-4-yl)-ethylammonium mesylate, 11.3 g (145.8 mmol) of calciumhydroxyde and 175 mL of DMF. The resulting suspension was heated to 30° C. and stirred for 30 min at this temperature. A solution of 13.4 g (77.6 mmol) of (S)-1-(2-chloroacetyl)-pyrrolidine-2-carbonitrile in 75 mL of DMF was added within 25 min and the dropping funnel was rinsed with 10 mL of DMF. The mixture was heated to 25° C. to 30° C. and stirred for 1 to 2 h at this temperature. The reaction mixture was cooled to 10° C. and treated with 175 mL of water at 10° C. to 30° C. The suspension was filtered over Speedex with suction and the filter cake was washed with 35 mL of water. The filtrate was extracted with 200 mL of methylenechloride. The layers were separated and the aqueous phase was extracted with 100 mL of methylenechloride. The organic layers were unified and twice washed with a total of 200 mL of aqueous NaCl 10% solution. The organic layer was treated with 8.3 g (85.5 mmol) of methanesulfonic acid. Methylenechloride was removed by distillation under normal pressure at a jacket temperature of max. 55° C. The resulting suspension was treated with 180 mL of methylenechloride, filtered with suction and the filter cake was twice washed with totally 30 mL of methylenechloride. The filtrate was concentrated under vacuum (550-35 mbar) at a jacket temperature of max. 50° C. The residue was treated with 175 mL of THF at 45° C. to 50° C., inoculated and again treated with 175 mL of 2-butanone. 65 mL of THF were distilled off under vacuum (340 mbar). The resulting suspension was cooled to 0° C. within 4 h and stirred at this temperature for at least 2 h. The precipitate was filtered with suction, the filter cake was washed with 50 mL of cold THF (0° C.) and dried under vacuum (50° C., 50 mbar) to afford 24.2 g (yield 73.9% starting from of (S)-1-(2-chloroacetyl)-pyrrolidine-2-carbonitrile, 95.7% (m/m) purity based on HPLC assay) of (S)-1-{[2-(5-Methyl-2-phenyl-oxazol-4-yl)-ethylamino]-acetyl}-pyrrolidine-2-carbonitrile mesylate as a colorless solid.

Example 17

5.0 g of (S)-1-{[2-(5-Methyl-2-phenyl-oxazol-4-yl)-ethylamino]-acetyl}pyrrolidine-2-carbonitrile mesylate were dissolved in 60 mL of dry 2-propanol at 60° C. After polishing filtration, the clear solution was stirred and linearly cooled from 60° C. to 5° C. within 1 h. The slurry was stirred for additional 4 h at 5° C., before the crystals were harvested by filtration. The colorless solid was rinsed with 10 mL of cold 2-propanol (0° C.) and dried in vacuum (5-20 mbar) at 25° C., yielding 4.4 g (89%) of (S)-1-{[2-(5-methyl-2-phenyl-oxazol-4-yl)-ethylamino]-acetyl}pyrrolidine-2-carbonitrile mesylate as crystalline polymorph A.

Example 18

5.0 g of (S)-1-{[2-(5-Methyl-2-phenyl-oxazol-4-yl)-ethylamino]-acetyl}pyrrolidine-2-carbonitrile mesylate were dissolved in a mixture of 47 g 2-propanol and 1.7 g water at 60° C. After polishing filtration, the solution was linearly cooled from 60° C. to 0° C. within 2 h. The slurry was stirred for additional 4 h at 0° C. After filtration, the colorless solid was rinsed with a cold (0° C.) mixture of 7.3 g 2-propanol and 0.23 g water. The reminder was dried in vacuum (5-20 mbar) at 40° C. for 16 h, yielding 4.3 g (85%) of (S)-1-{[2-(5-methyl-2-phenyl-oxazol-4-yl)-ethylamino]-acetyl}pyrrolidine-2-carbonitrile mesylate as water-free crystalline polymorph B. Before analysis, the crystals were optionally exposed to ambient atmosphere (23° C., 40% relative humidity for 16 h).

Example 19

5.0 g of dry (S)-1-{[2-(5-methyl-2-phenyl-oxazol-4-yl)-ethylamino]-acetyl}pyrrolidine-2-carbonitrile mesylate was slurried in 60 mL of 2-butanone at 22° C. for 14 days. Then the crystals were harvested by filtration and rinsed with 10 mL of 2-butanone. The crystals were dried in vacuum (5-20 mbar) at 22° C. for 16 h, yielding 4.6 g (92%) of (S)-1-{[2-(5-methyl-2-phenyl-oxazol-4-yl)-ethylamino]-acetyl}pyrrolidine-2-carbonitrile mesylate as crystalline polymorph C.

Example 20

When performing the crystallization according to example 1 repeatedly, polymorph D can be obtained in some minor number of cases. Crystalline polymorph D obtained in such a way can then be used for seeding in the procedure given below. Alternatively, crude crystalline polymorph D can be obtained by wet grinding of crystalline polymorph B in dry isopropanol, which can then be used for seeding in the procedure given below.

10.0 g of (S)-1-{[2-(5-Methyl-2-phenyl-oxazol-4-yl)-ethylamino]-acetyl}pyrrolidine-2-carbonitrile mesylate were dissolved in 120 mL of dry 2-propanol at 60° C. After polishing filtration, the clear solution was stirred and linearly cooled from 60° C. to 5° C. within 1 h. At 55° C. the crystallization was seeded with 10 mg of crystalline polymorph D. The slurry was stirred for additional 4 h at 5° C., before the crystals were harvested by filtration. The colorless solid was rinsed with 20 mL of cold 2-propanol (0° C.) and dried in vacuum (5-20 mbar) at 25° C., yielding 9.5 g (95%) of (S)-1-{[2-(5-methyl-2-phenyl-oxazol-4-yl)-ethylamino]-acetyl}pyrrolidine-2-carbonitrile mesylate as crystalline polymorph D.

Example 21

Film coated tablets containing the following ingredients can be manufactured in a conventional manner:

| Ingredients | Per tablet | |
|---|---|---|
| Kernel: | | |
| Active ingredient | 50.0 mg | 200.0 mg |
| Lactose hydrous | 58.5 mg | 125.5 mg |
| Povidone K30 | 10 mg | 20.0 mg |
| Magnesium stearate | 1.5 mg | 4.5 mg |
| (Kernel Weight) | 120.0 mg | 350.0 mg |

-continued

| Ingredients | Per tablet | |
|---|---|---|
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Titan dioxide | 0.8 mg | 1.6 mg |

The active ingredient is sieved and mixed with lactose and the mixture is granulated with a solution of polyvinylpyrrolidone in water or ethanol by fluid bed granulation. The granulate is mixed with sodium starch glycolate and magnesium stearate and compressed to yield kernels of 120 or 350 mg respectively. The kernels are lacquered with an aqueous solution/suspension of the above mentioned film coat.

Example 22

Capsules containing the following ingredients can be manufactured in a conventional manner:

| Ingredients | Per capsule |
|---|---|
| Active ingredient | 25.0 mg |
| Lactose | 170.0 mg |
| Talc | 5.0 mg |

The components are sieved and mixed and filled into capsules of size 2.

It is to be understood that the invention is not limited to the particular embodiments of the invention described above, as variations of the particular embodiments may be made and still fall within the scope of the appended claims.

What is claimed is:

1. A crystalline polymorph of (S)-1-{[2-(5-Methyl-2-phenyl-oxazol-4-yl)-ethylamino]-acetyl}-pyrrolidine-2-carbonitrile mesylate, comprising an X-ray powder diffraction pattern with characteristic peaks expressed in degrees 2-theta at approximately:

| degree 2-theta |
|---|
| 5.4 |
| 13.3 |
| 15.0 |
| 17.1 |
| 19.5 |
| 21.1 |
| 21.4 |
| 26.9. |

2. The crystalline polymorph according to claim 1, comprising the x-ray powder diffraction pattern shown in FIG. 1.

3. The crystalline polymorph according to claim 1, comprising an IR absorption spectrum having characteristic peaks expressed in $cm^{-1}$ at approximately 3503 $cm^{-1}$, 2747 $cm^{-1}$, 2649 $cm^{-1}$, 2477 $cm^{-1}$, 2240 $cm^{-1}$, 1666 $cm^{-1}$, 1638 $cm^{-1}$, 1552 $cm^{-1}$, 1427 $cm^{-1}$, 1377 $cm^{-1}$, 1360 $cm^{-1}$, 1334 $cm^{-1}$, 1305 $cm^{-1}$, 1270 $cm^{-1}$, 1161 $cm^{-1}$, 1088 $cm^{-1}$, 1070 $cm^{-1}$, 1047 $cm^{-1}$, 1024 $cm^{-1}$, 994 $cm^{-1}$, 966 $cm^{-1}$, 950 $cm^{-1}$, 915 $cm^{-1}$, 878 $cm^{-1}$, 838 $cm^{-1}$, 805 $cm^{-1}$, 778 $cm^{-1}$, 715 $cm^{-1}$, 696 $cm^{-1}$, 689 $cm^{-1}$, 650 $cm^{-1}$.

4. The crystalline polymorph according to claim 3, comprising the IR absorption spectrum shown in FIG. 2.

5. A method for the treatment of diabetes, non-insulin dependent diabetes mellitus, impaired glucose tolerance, bowl disease, colitis ulcerosa, morbus crohn, obesity, or metabolic syndrome, comprising the step of administering a therapeutically effective amount of the crystalline polymorph according to claim 1 to a human being or animal in need thereof.

* * * * *